United States Patent
Moon et al.

(10) Patent No.: US 6,825,190 B2
(45) Date of Patent: Nov. 30, 2004

(54) PROTEIN KINASE INHIBITORS AND USES THEREOF

(75) Inventors: Young-Choon Moon, Belle Mead, NJ (US); Jeremy Green, Burlington, MA (US); Robert Davies, Arlington, MA (US); Deborah Choquette, Medford, MA (US); Albert Pierce, Cambridge, MA (US); Mark Ledeboer, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/172,888

(22) Filed: Jun. 14, 2002

(65) Prior Publication Data

US 2004/0009996 A1 Jan. 15, 2004

Related U.S. Application Data

(60) Provisional application No. 60/298,646, filed on Jun. 15, 2001.

(51) Int. Cl.[7] .................... C07D 413/04; A61K 31/506; A61P 3/10; A61P 25/18; A61P 37/06
(52) U.S. Cl. .................... 514/218; 514/235.8; 514/275; 544/331; 544/122; 540/575
(58) Field of Search ................. 544/331, 122; 540/575; 514/275, 218, 235.8

(56) References Cited

U.S. PATENT DOCUMENTS 6,093,716 A  7/2000  Davis et al. ............... 514/253

FOREIGN PATENT DOCUMENTS

| WO | WO 97/19065 A | 5/1997 |
| WO | WO 00/78731 A | 12/2000 |
| WO | WO 01/00207 A | 1/2001 |
| WO | WO 01/00214 A | 1/2001 |
| WO | WO 01/12621 A | 2/2001 |
| WO | WO 01/29009 A | 4/2001 |
| WO | WO 01/72745 A | 10/2001 |

OTHER PUBLICATIONS

Duhe et al. Cell Biochem. Biophys. 34(1): 17–59, 2001.*
Rane et al., Oncogene 19(49): 5662–79, 2000.*
Kim et al., Curr. Opin Genet Dev. 10(5): 508–514, 2000.*
J. Zimmermann et al., "Potent and Selective Inhibitors of the Abl–Kinase: Phenylamino–Pyrimidine (PAP) Derivatives," Bioorg. Med. Chem. Lett., 7, pp. 187–192 (1997).

* cited by examiner

Primary Examiner—Venkataraman Balasubramanian
(74) Attorney, Agent, or Firm—Andrea L.C. Robidoux; Choate, Hall & Stewart

(57) ABSTRACT

Described herein are benzisoxazole compounds of formula I:

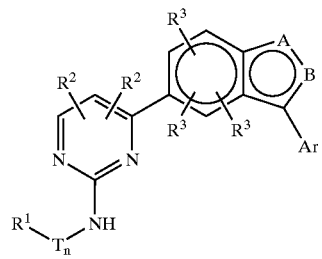

or a pharmaceutically acceptable derivative or prodrug thereof, wherein A-B is N—O or O—N; Ar is an optionally substituted $C_{5-10}$ aryl group; $R^1$ is hydrogen or an optionally substituted group selected from $C_{1-10}$ aliphatic, $C_{5-10}$ aryl, $C_{6-12}$ aralkyl, $C_{3-10}$ heterocyclyl, or $C_{4-12}$ heterocyclylalkyl; and T, n, $R^2$ and $R^3$ are as described in the specification. These compounds are inhibitors of protein kinases, particularly inhibitors of GSK-3 and JAK mammalian protein kinases. The invention also provides pharmaceutically acceptable compositions comprising the compounds of the invention and methods of utilizing those compounds and compositions in the treatment of various protein kinase mediated disorders.

13 Claims, No Drawings

PROTEIN KINASE INHIBITORS AND USES THEREOF

CROSS REFERENCE TO RELATED APPLICATIONS

This applications claims the benefit of United States Provisional Application No. 60/298,646, filed Jun. 15, 2001. The entire teaching of this application is incorporated herein by reference.

FIELD OF THE INVENTION

The present invention is in the field of medicinal chemistry and relates to compounds that are protein kinase inhibitors, compositions comprising such compounds and methods of use. More particularly, the compounds are inhibitors of GSK-3 and JAK and are useful for treating disease states, such as diabetes and Alzheimer's disease, that are alleviated by GSK-3 inhibitors, and allergic disorders, autoimmune diseases, and conditions associated with organ transplantation that are alleviated by JAK inhibitors.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is the protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor $\alpha$ (TNF-$\alpha$)), and growth factors (e.g. granulocyte macrophage-colony-stimulating factor (GM-CSF), and fibroblast growth factor (FGF)). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many disease states are associated with abnormal cellular responses triggered by protein kinase-mediated events. These diseases include autoimmune diseases, inflammatory diseases, metabolic diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents. A challenge has been to find protein kinase inhibitors that act in a selective manner. Since there are numerous protein kinases that are involved in a variety of cellular responses, non-selective inhibitors may lead to unwanted side effects.

Glycogen synthase kinase-3 (GSK-3) is a serine/threonine protein kinase comprised of $\alpha$ and $\beta$ isoforms that are each encoded by distinct genes [Coghlan et al., *Chemistry & Biology*, 7, 793–803 (2000); Kim and Kimmel, *Curr. Opinion Genetics Dev.*, 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These include glycogen synthase which is the rate limiting enzyme necessary for glycogen synthesis, the microtubule associated protein Tau, the gene transcription factor $\beta$-catenin, the translation initiation factor e1F2B, as well as ATP citrate lyase, axin, heat shock factor-1, c-Jun, c-Myc, c-Myb, CREB, and CEPB$\alpha$. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS*, 93, 8455–9 (1996); Cross et al., *Biochem. J.*, 303, 21–26 (1994); Cohen, *Biochem. Soc. Trans.*, 21, 555–567 (1993); Massillon et al., *Biochem J.* 299, 123–128 (1994)]. However, in a diabetic patient where the insulin response is impaired, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known $\beta$-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077–86 (1994); Brownlees et al., *Neuroreport* 8, 3251–55 (1997)]. Therefore, it is believed that GSK-3 activity may promote generation of the neurofibrillary tangles and the progression of Alzheimer's disease.

Another substrate of GSK-3 is $\beta$-catenin which is degradated after phosphorylation by GSK-3. Reduced levels of $\beta$-catenin have been reported in schizophrenic patients and have also been associated with other diseases related to increase in neuronal cell death [Zhong et al., *Nature*, 395, 698–702 (1998); Takashima et al., *PNAS*, 90, 7789–93 (1993); Pei et al., *J. Neuropathol. Exp*, 56, 70–78 (1997); Smith et al., *Bio-org. Med. Chem.* 11, 635–639 (2001)].

Small molecule inhibitors of GSK-3 have recently been reported [WO 99/65897 (Chiron) and WO 00/38675 (SmithKline Beecham)].

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed

[Frank Mol. Med. 5: 432–456 (1999) & Seidel, et al, Oncogene 19: 2645–2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, Blood 96: 2172–2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, Nature 346: 274–276 (1990) & Galli, N. Engl. J. Med., 328: 257–265 (1993)]. A crucial role for JAK3 in IgE receptor-mediated mast cell responses in vitro and in vivo has been established [Malaviya, et al, Biochem. Biophys. Res. Commun. 257: 807–813 (1999)]. In addition, the prevention of type I hypersensitivity reactions, including anaphylaxis, mediated by mast cell-activation through inhibition of JAK3 has also been reported [Malaviya et al, J. Biol. Chem. 274:27028–27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immunosuppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, transpl. proc. 33: 3268–3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner, et al, J. Immunol. 164: 3894–3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu, et al, Biochem. Biophys. Res. Commun. 267: 22–25 (2000)].

Signal transducer and activator of transcription (STAT) proteins are activated by, among others, the JAK family kinases. Results from a recent study suggested the possibility of intervention in the JAK/STAT signaling pathway by targeting JAK family kinases with specific inhibitors for the treatment of leukemia [Sudbeck, et al, Clin. Cancer Res. 5: 1569–1582 (1999)]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, EMBO J. 17: 5321–5333 (1998)].

Inhibition of JAK3 and TYK2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, Proc. Nat. Acad. Sci. U.S.A. 94: 6764–6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, J. Immunol. 159: 5206–5210 (1997)]. In addition, IL-6-mediated STAT3 activation was blocked by an inhibitor of JAK, leading to sensitization of myeloma cells to apoptosis [Catlett-Falcone, et al, Immunity 10:105–115 (1999)].

There is a continued need to find new therapeutic agents to treat human diseases. Accordingly, there is a great need to develop inhibitors of GSK-3 and JAK protein kinases that are useful in treating various diseases or conditions associated with GSK-3 and JAK activation, particularly given the inadequate treatments currently available for the majority of these disorders.

DESCRIPTION OF THE INVENTION

It has now been found that compounds of this invention and pharmaceutical compositions thereof are effective as protein kinase inhibitors, particularly as inhibitors of GSK-3 and JAK. These compounds have the general formula I:

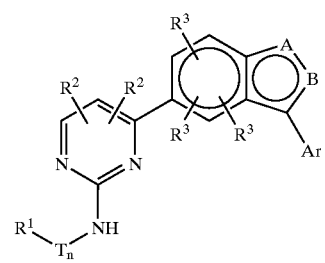

or a pharmaceutically acceptable derivative or prodrug thereof, wherein:

A-B is N—O or O—N;
Ar is an optionally substituted $C_{5-10}$ aryl group;
T is a $C_{1-4}$ alkylidene chain wherein one or two methylene units of T are optionally and independently replaced by O, NR, S, C(O), C(O)NR, NRC(O)NR, $SO_2$, $SO_2NR$, $NRSO_2$, $NRSO_2NR$, $CO_2$, OC(O), $NRCO_2$, or OC(O)NR;
n is zero or one;
$R^1$ is hydrogen or an optionally substituted group selected from $C_{1-10}$ aliphatic, $C_{5-10}$ aryl, $C_{6-12}$ aralkyl, $C_{3-10}$ heterocyclyl, or $C_{4-12}$ heterocyclylalkyl;
each $R^2$ is independently selected from R, halo, CN, OR, $N(R)_2$, SR, C(=O)R, $CO_2R$, $CONR_2$, NRC(=O)R, $NRCO_2(C_{1-6}$ aliphatic), OC(=O)R, $SO_2R$, S(=O)R, $SO_2NR_2$, or $NRSO_2(C_{1-6}$ aliphatic);
each $R^3$ is independently selected from R, halo, CN, OR, $N(R)_2$, SR, C(=O)R, $CO_2R$, $CONR_2$, NRC(=O)R, $NRCO_2(C_{1-6}$ aliphatic), OC(=O)R, $SO_2R$, S(=O)R, $SO_2NR_2$, or $NRSO_2(C_{1-6}$ aliphatic); and
each R is independently selected from hydrogen, a $C_{1-8}$ aliphatic group, or two R on the same nitrogen are taken together with the nitrogen to form a 4–8 membered heterocyclic ring having 1–3 heteroatoms selected from nitrogen, oxygen or sulfur.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$–$C_{10}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include substituted or unsubstituted linear or branched alkyl, alkenyl, or alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen or sulfur and includes any oxidized form of nitrogen and sulfur, and the quaternized form of any basic nitrogen. Also, the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl). It is understood that the compounds of this invention are limited to those that can exist in nature as stable chemical compounds.

The term "unsaturated", as used herein, means that a moiety has one or more units of unsaturation, and includes aryl rings.

The term "aryl", used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic", as used herein means non-aromatic, monocyclic, bicyclic, or tricyclic ring systems having five to fourteen ring members in which one or more ring members is a heteroatom, wherein each ring in the system contains 3 to 7 ring members.

The term "heteroaryl", used alone or as part of a larger moiety as in "heteroarylalkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are independently selected from halogen, —$R^o$, —$OR^o$, —$O(CH_2)_yR^o$, —$SR^o$, 1,2-methylene-dioxy, 1,2-ethylenedioxy, phenyl (Ph) optionally substituted with $R^o$, —O(Ph) optionally substituted with $R^o$, —$CH_2$(Ph) optionally substituted with $R^o$, —$CH_2CH_2$(Ph) optionally substituted with $R^o$, 5–8 membered heteroaryl optionally substituted with $R^o$, 5–8 membered heterocycle optionally substituted with $R^o$, —$NO_2$, —CN, —$N(R^o)_2$, —$N(R^o)(CH_2)_yR^o$, —$NR^oC(O)R^o$, —$NR^oC(O)N(R^o)_2$, —$NR^oCO_2R^o$, —$NR^oNR^oC(O)R^o$, —$NR^oNR^oC(O)N(R^o)_2$, —$NR^oNR^oCO_2R^o$, —C(O)C(O)$R^o$, —C(O)$CH_2$C(O)$R^o$, —$CO_2R^o$, —C(O)$R^o$, —C(O)N($R^o$)$_2$, —OC(O)N($R^o$)$_2$, —$S(O)_2R^o$, —$SO_2N(R^o)_2$, —S(O)$R^o$, —$NR^oSO_2N(R^o)_2$, —$NR^oSO_2R^o$, —C(=S)N($R^o$)$_2$, —C(=NH)—N($R^o$)$_2$, or —$(CH_2)_yNHC(O)R^o$, wherein each $R^o$ is independently selected from hydrogen, optionally substituted $C_{1-6}$ aliphatic, phenyl, —O(Ph), or —$CH_2$(Ph), wherein y is 0–6. When $R^o$ is a $C_{1-6}$ aliphatic group or a phenyl ring, it may be substituted with one or more substituents selected from —$NH_2$, —NH($C_{1-4}$ aliphatic) —N($C_{1-4}$ aliphatic)$_2$, —S(O)($C_{1-4}$ aliphatic), —$SO_2$($C_{1-4}$ aliphatic), halogen, —($C_{1-4}$ aliphatic), OH, —O($C_{1-4}$ aliphatic), $NO_2$, CN, $CO_2H$, —$CO_2$($C_{1-4}$ aliphatic), —O(halo $C_{1-4}$ aliphatic), or -halo ($C_{1-4}$ aliphatic); wherein each $C_{1-4}$ aliphatic is unsubstituted.

An aliphatic group or a non-aromatic heterocyclic ring may contain one or more substituents. A saturated carbon of an aliphatic group or of a non-aromatic heterocyclic ring may have one or more substituents. Suitable substituents on the saturated carbon of an aliphatic group or of a non-aromatic heterocyclic ring are selected from those listed above for the unsaturated carbon of an aryl or heteroaryl group as well as the following: =O, =S, =NNHR*, =NN($R^*$)$_2$, =N—, =NNHC(O)R*, =NNCO$_2$(alkyl), =NNHSO$_2$(alkyl), or =NR*, where each R* is independently selected from hydrogen or an optionally substituted $C_{1-6}$ aliphatic. When R* is $C_{1-6}$ aliphatic, it may be substituted with one or more substituents independently selected from —$NH_2$, —NH($C_{1-4}$ aliphatic), —N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo ($C_{1-4}$ aliphatic); wherein each $C_{1-4}$ aliphatic is unsubstituted.

Substituents on the nitrogen of a non-aromatic heterocyclic ring are selected from —$R^+$, —N($R^+$)$_2$, —C(O)$R^+$, —$CO_2R^+$, —C(O)C(O)$R^+$, —C(O)$CH_2$C(O)$R^+$, —$SO_2R^+$, —$SO_2N(R^+)_2$, —C(=S)N($R^+$)$_2$, —C(=NH)—N($R^+$)$_2$, or —$NR^+SO_2R^+$; wherein each $R^+$ is independently selected from hydrogen, an optionally substituted $C_{1-6}$ aliphatic, optionally substituted phenyl, optionally substituted —O(Ph), optionally substituted —$CH_2$(Ph), optionally substituted —$CH_2CH_2$(Ph), or an unsubstituted 5–6 membered heteroaryl or heterocyclic ring. When $R^+$ is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo($C_{1-4}$ aliphatic); wherein each $C_{1-4}$ aliphatic is unsubstituted.

The term "alkylidene chain" refers to a straight or branched carbon chain that may be fully saturated or have one or more units of unsaturation and has two points of attachment to the rest of the molecule.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

One embodiment of the present invention relates to compounds which are 2,1-benzisoxazoles, represented by formula I-A shown below. Another embodiment of this invention relates to compounds which are 1,2-benzisoxazoles, represented by formula I-B shown below:

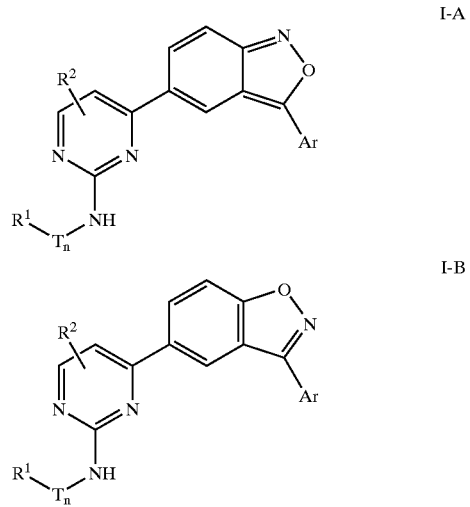

wherein Ar, T, n, $R^1$, and $R^2$ are as described above for formula I.

Ar is preferably a substituted or unsubstituted five or six-membered aromatic ring having zero to two ring heteroatoms selected from nitrogen, sulfur or oxygen. A more preferred Ar is a substituted or unsubstituted six-membered aromatic ring having zero to two ring nitrogens. Most preferably, Ar group is a substituted or unsubstituted phenyl ring. Preferably, Ar is substituted with one or more substituents independently selected from $C_{1-10}$ aliphatic, $C_{5-10}$ aryl, $C_{6-12}$ aralkyl, $C_{3-10}$ heterocyclyl, $C_{4-12}$ heterocyclylalkyl, halo, CN, OR, $N(R)_2$, SR, C(=O)R, $CO_2R$, $CONR_2$, NRC(=O)R, $NRCO_2(C_{1-6}$ aliphatic), OC(=O)R, $SO_2R$, S(=O)R, $SO_2NR_2$, or $NRSO_2(C_{1-6}$ aliphatic), or two substituents on adjacent positions are optionally taken together with their intervening atoms to form a fused 5–8 membered unsaturated or partially unsaturated ring having zero to two heteroatoms selected from nitrogen, oxygen or sulfur; wherein R is as described above for formula I.

$R^1$ is preferably hydrogen or an aryl ring, such as a phenyl or pyridyl ring. Optional substituents on $R^1$ are independently selected from halogen, —R, —OR, —OH, —SH, —SR, protected OH (such as acyloxy), —$NO_2$, —CN, —$NH_2$, —NHR, —$N(R)_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SO$_2NH_2$, —S(O)R, —SO$_2$NHR, or —NHS(O)$_2$R, where R is a $C_{1-6}$ aliphatic group or a substituted $C_{1-6}$ aliphatic group, preferably having one to three carbons. A particularly preferred substituent on the $C_{1-6}$ aliphatic group is —SO$_2NH_2$.

$R^2$ is preferably hydrogen or a $C_{1-4}$ alkyl group, most preferably hydrogen.

$R^3$ is preferably hydrogen, halo, O($C_{1-4}$ alkyl), or a $C_{1-4}$ alkyl group. Most preferably $R^3$ is hydrogen. Representative examples of compounds of formula I-A are shown below in Table 1.

TABLE 1

Examples of Compounds of formula I-A

| No. | Structure |
|---|---|
| I-A1 | 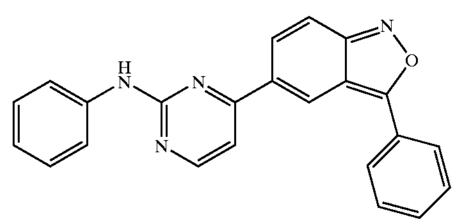 |

TABLE 1-continued
Examples of Compounds of formula I-A
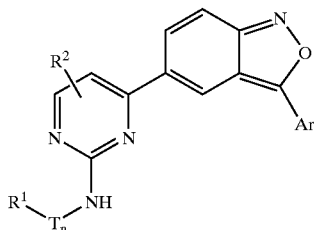
| No. | Structure |
|---|---|
| I-A2 | 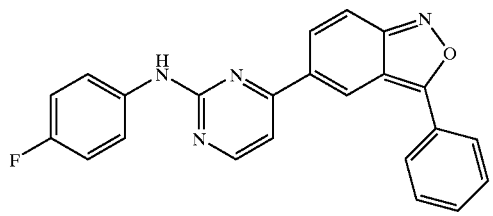 |
| I-A3 | 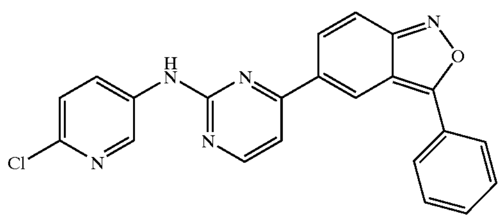 |
| I-A4 | 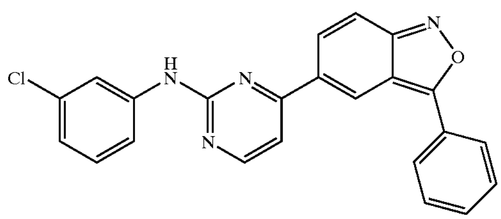 |
| I-A5 | 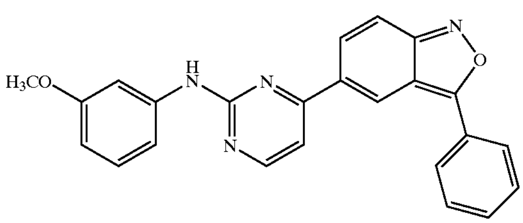 |
| I-A6 | 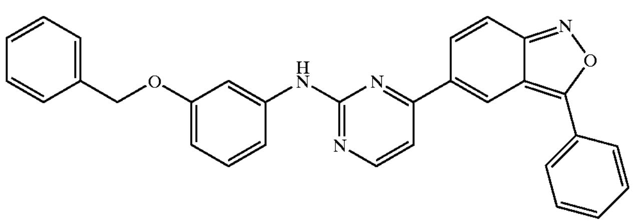 |

TABLE 1-continued
Examples of Compounds of formula I-A
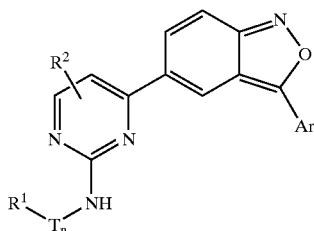
| No. | Structure |
|---|---|
| I-A7 | 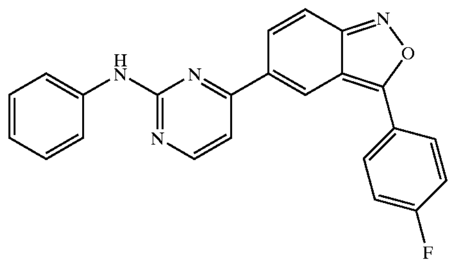 |
| I-A8 | 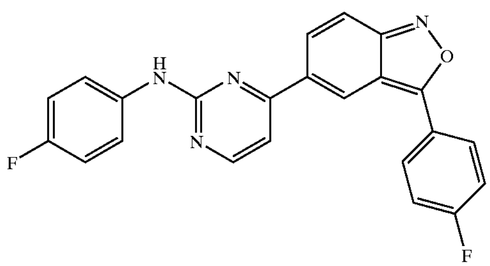 |
| I-A9 | 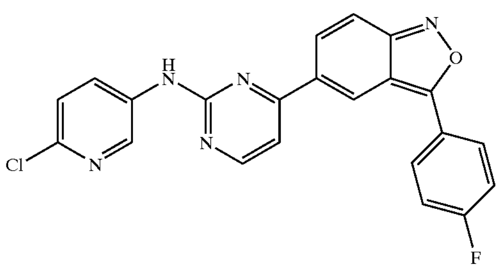 |
| I-A10 | 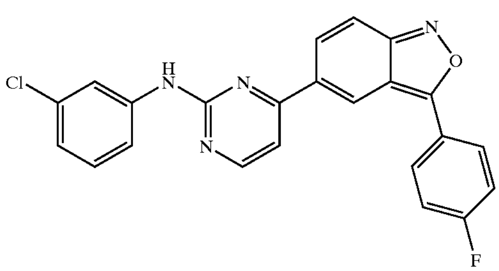 |

TABLE 1-continued
Examples of Compounds of formula I-A
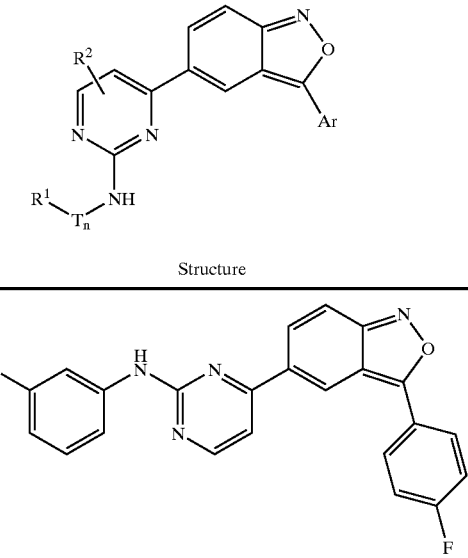
| No. | Structure |
|---|---|
| I-A11 | 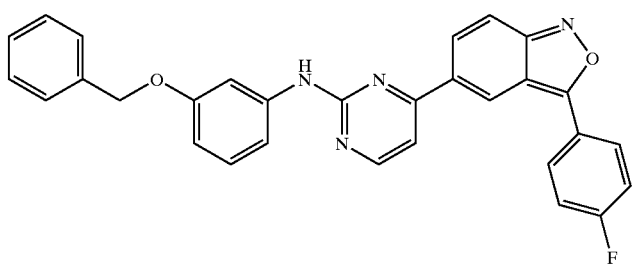 |
| I-A12 | 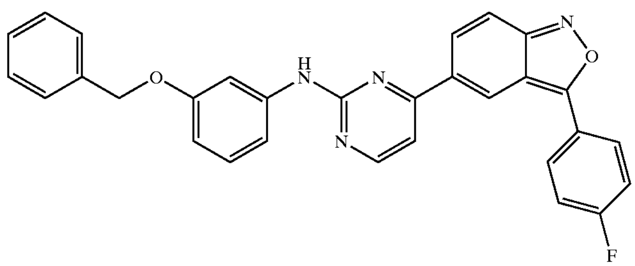 |
| I-A13 | 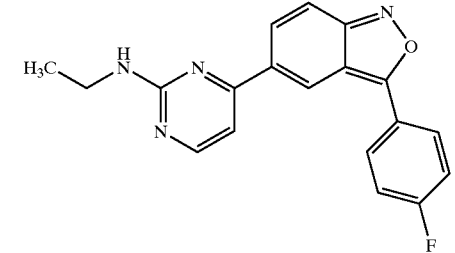 |
| I-A14 | 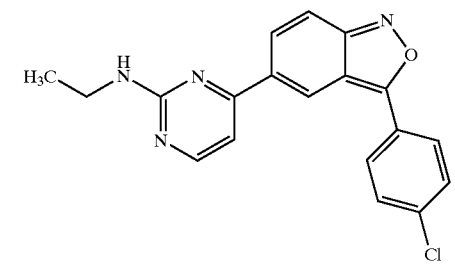 |
| I-A15 | 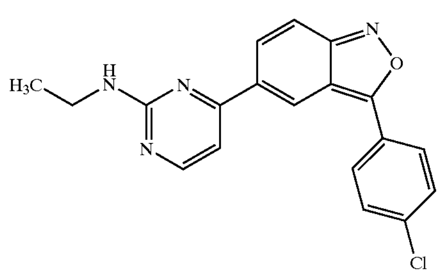 |

TABLE 1-continued
Examples of Compounds of formula I-A
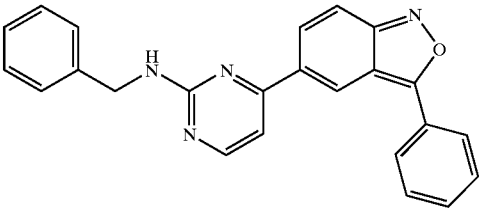
| No. | Structure |
|---|---|
| I-A16 | 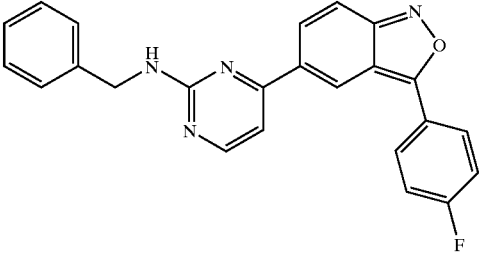 |
| I-A17 | 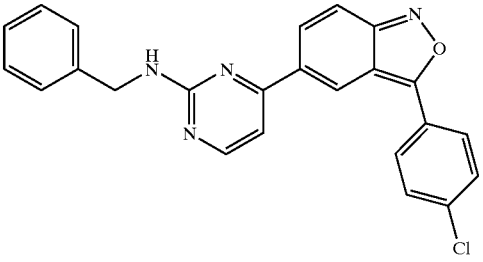 |
| I-A18 | 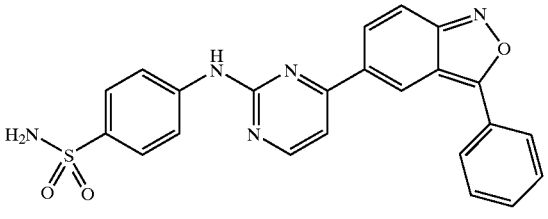 |
| I-A19 | 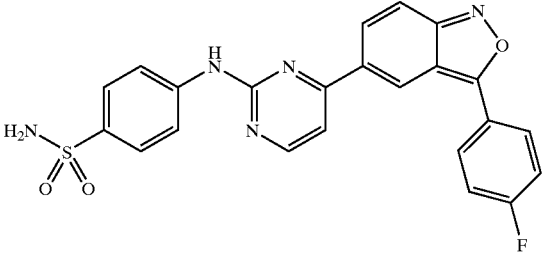 |
| I-A20 | 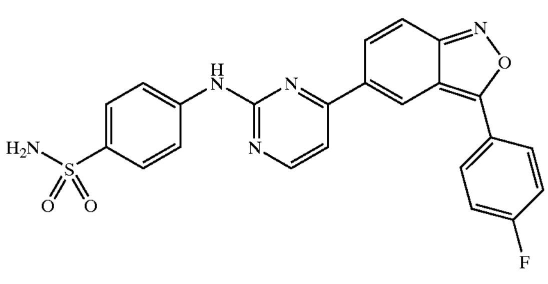 |

TABLE 1-continued
Examples of Compounds of formula I-A
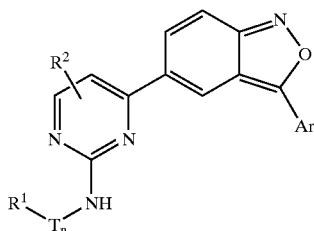
| No. | Structure |
| --- | --- |
| I-A21 | 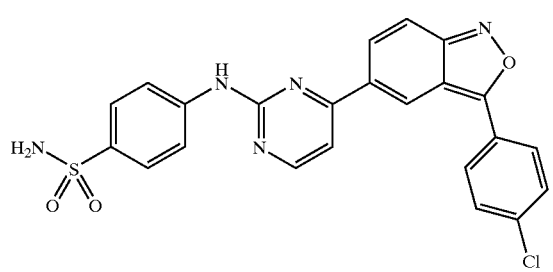 |
| I-A22 | 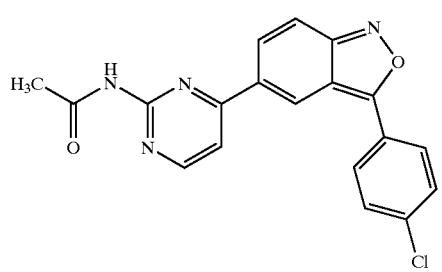 |
| I-A23 | 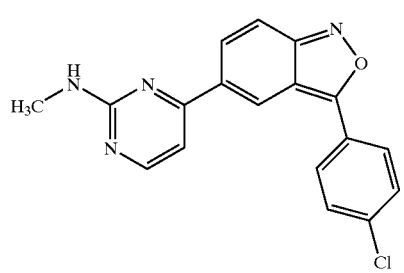 |
| I-A24 | 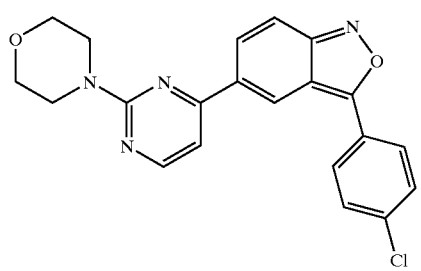 |

TABLE 1-continued
Examples of Compounds of formula I-A
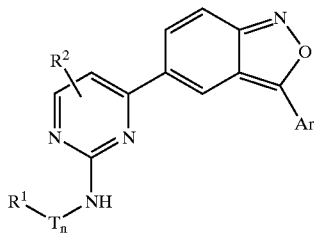
| No. | Structure |
|---|---|
| I-A25 | 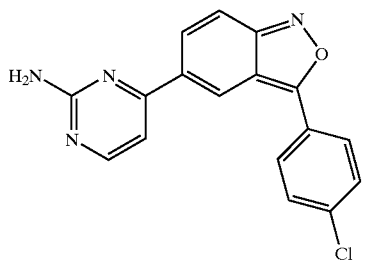 |
| I-A26 | 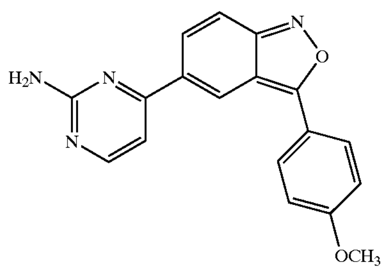 |
| I-A27 | 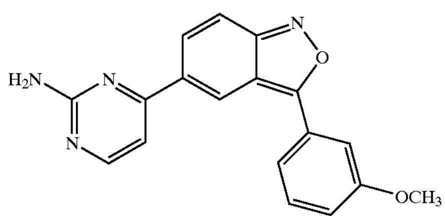 |
| I-A28 | 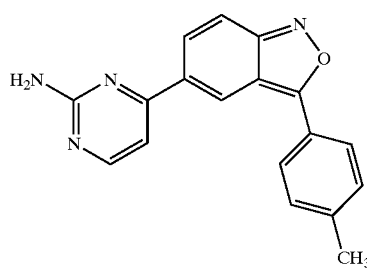 |
| I-A29 | 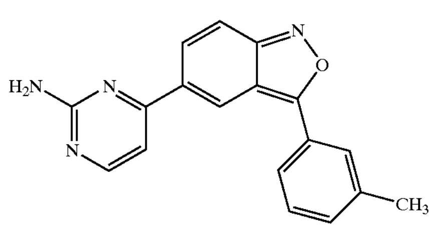 |

TABLE 1-continued
Examples of Compounds of formula I-A
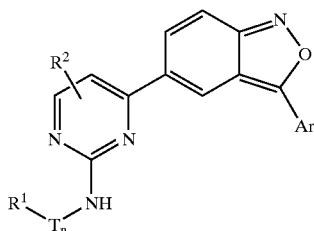
| No. | Structure |
|---|---|
| I-A30 | 4-(2-amino-pyrimidin-4-yl)-3-(4-fluorophenyl)-2,1-benzisoxazole |
| I-A31 | 5-(2-amino-pyrimidin-4-yl)-3-(3-fluorophenyl)-2,1-benzisoxazole |
| I-A32 | 5-(2-amino-pyrimidin-4-yl)-3-(4-piperidin-1-yl-phenyl)-2,1-benzisoxazole |
| I-A33 | 5-(2-amino-pyrimidin-4-yl)-3-(3-piperidin-1-yl-phenyl)-2,1-benzisoxazole |

TABLE 1-continued
Examples of Compounds of formula I-A
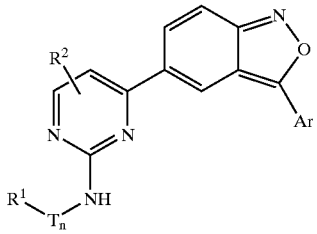
| No. | Structure |
|---|---|
| I-A34 | 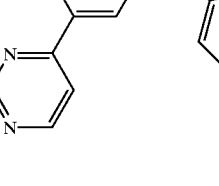 |
| I-A35 | 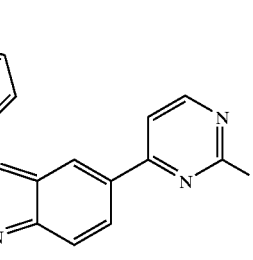 |
| I-A36 | 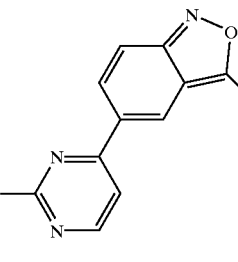 |
| I-A37 | 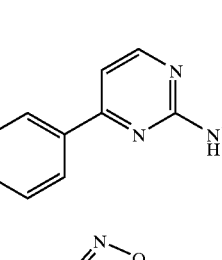 |
| I-A38 | 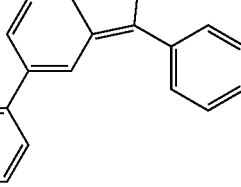 |

TABLE 1-continued
Examples of Compounds of formula I-A
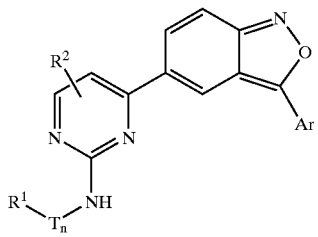
| No. | Structure |
|---|---|
| I-A39 | 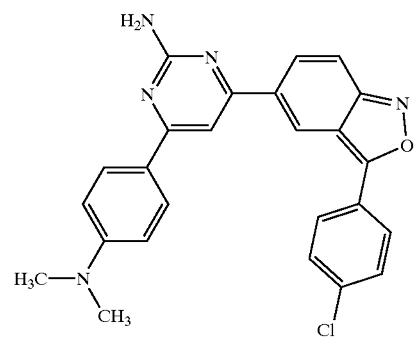 |
| I-A40 | 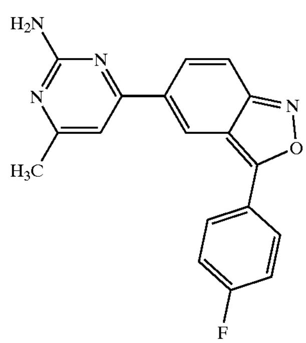 |
| I-A41 | 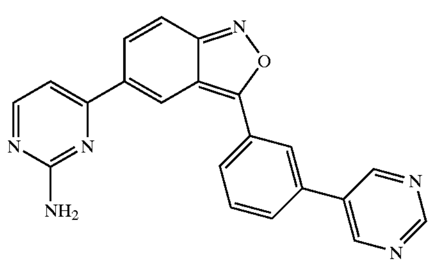 |
| I-A42 | 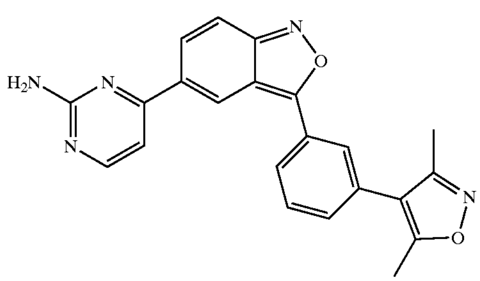 |

TABLE 1-continued
Examples of Compounds of formula I-A
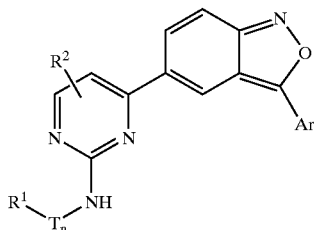
| No. | Structure |
|---|---|
| I-A43 | 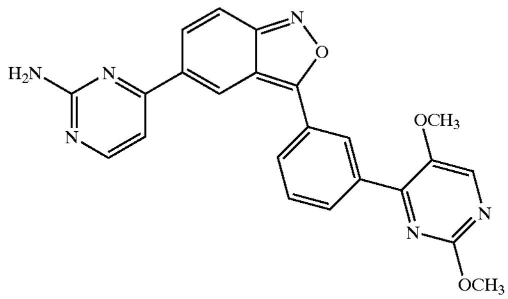 |
| I-A44 | 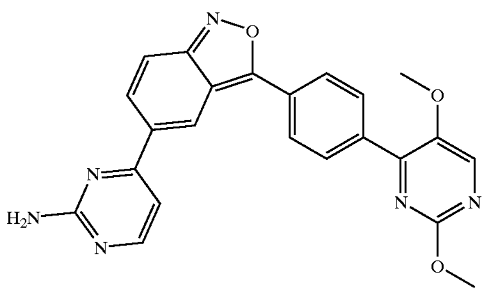 |
| I-A45 | 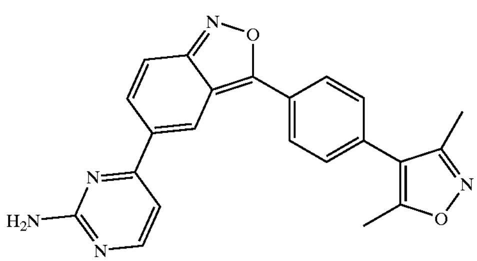 |
| I-A46 | 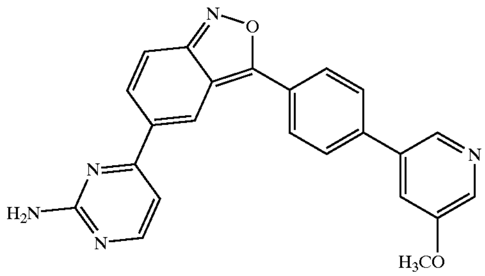 |

TABLE 1-continued
Examples of Compounds of formula I-A
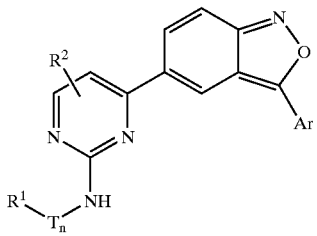
| No. | Structure |
|---|---|
| I-A47 | 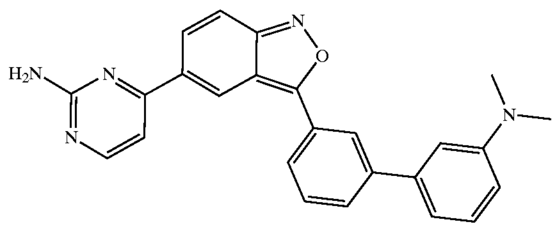 |
| I-A48 | 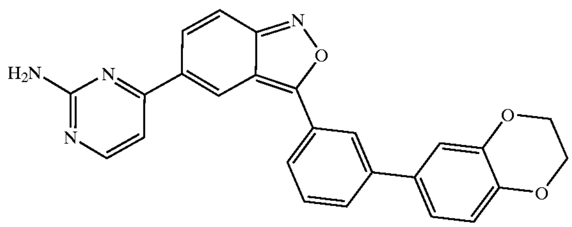 |
| I-A49 | 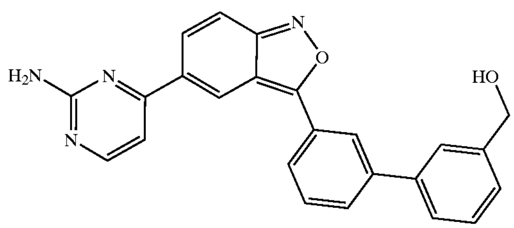 |
| I-A50 | 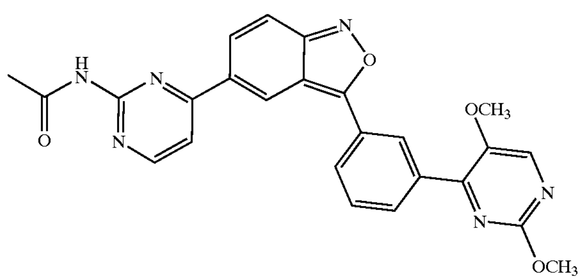 |
| I-A51 | 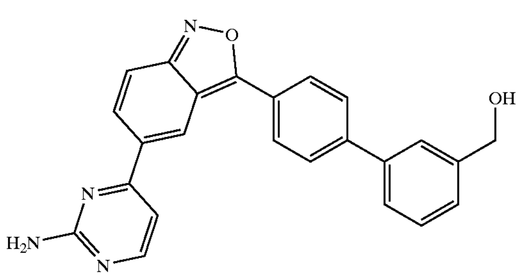 |

TABLE 1-continued
Examples of Compounds of formula I-A
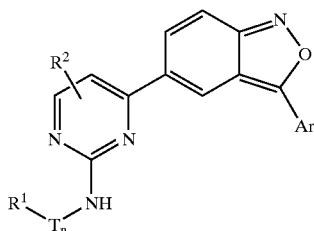
| No. | Structure |
|---|---|
| I-A52 | 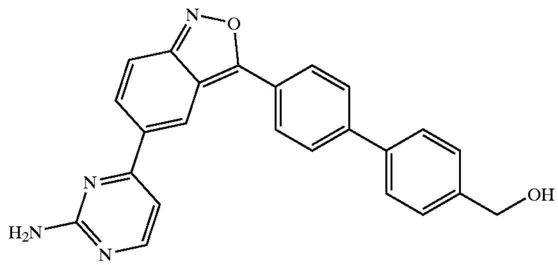 |
| I-A53 | 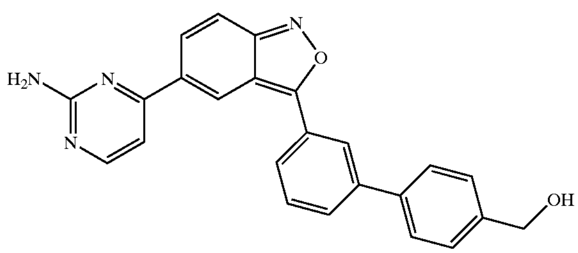 |
| I-A54 | 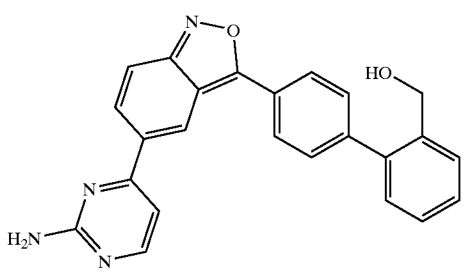 |
| I-A55 | 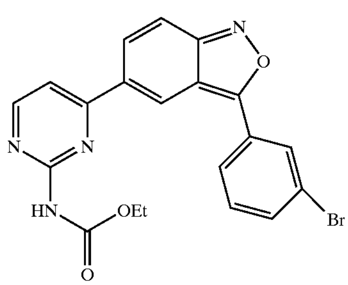 |

TABLE 1-continued
Examples of Compounds of formula I-A
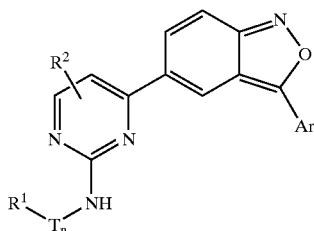
| No. | Structure |
|---|---|
| I-A56 | 3-(3-bromophenyl)-benzisoxazole-pyrimidine-thiophene-2-carboxamide |
| I-A57 | 3-(3-bromophenyl)-benzisoxazole-pyrimidine-furan-2-carboxamide |
| I-A58 | 3-(3-bromophenyl)-benzisoxazole-pyrimidine-phenoxyacetamide |
| I-A59 | 3-(3-bromophenyl)-benzisoxazole-pyrimidine-2-chloroethyl carbamate |

TABLE 1-continued
Examples of Compounds of formula I-A
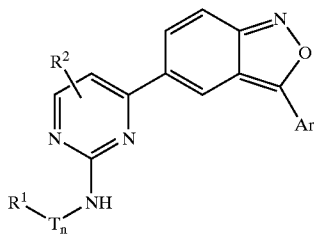
| No. | Structure |
|---|---|
| I-A60 | 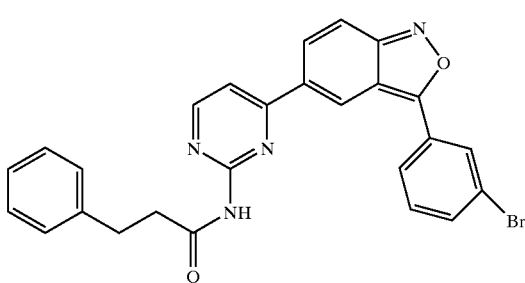 |
| I-A61 | 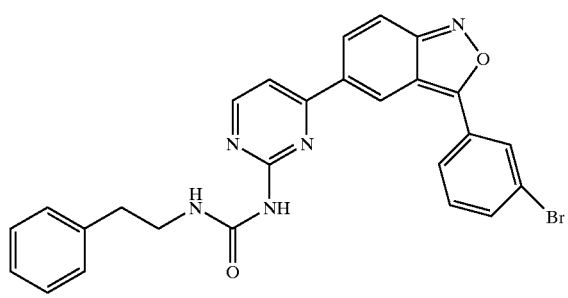 |
| I-A62 | 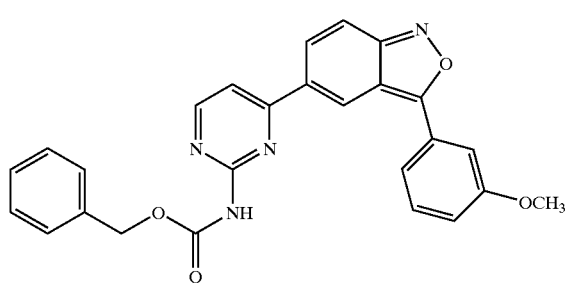 |
| I-A63 | 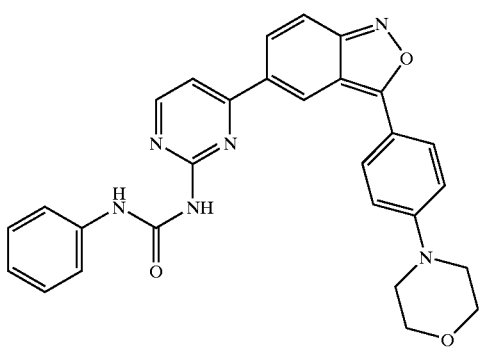 |

TABLE 1-continued
Examples of Compounds of formula I-A
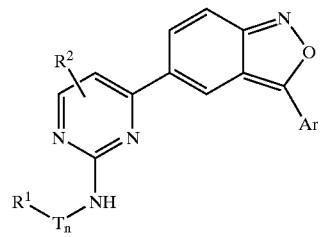
| No. | Structure |
|---|---|
| I-A64 | 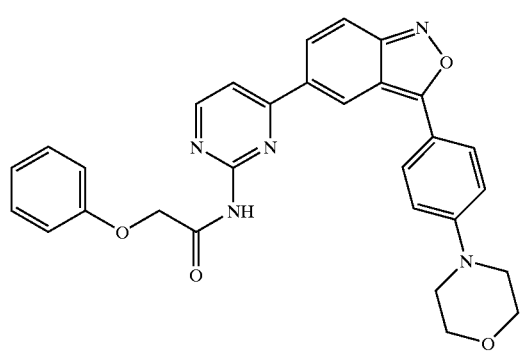 |
| I-A65 | 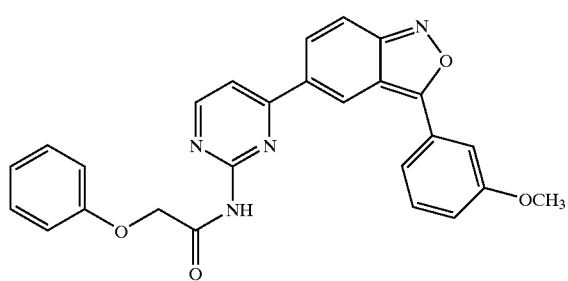 |
| I-A66 | 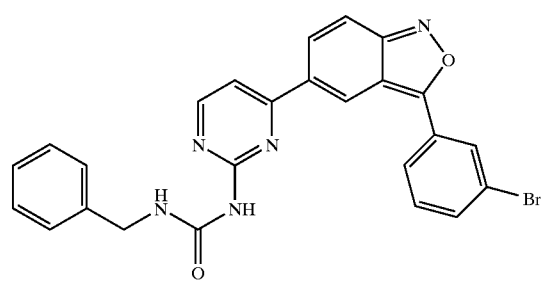 |
| I-A67 | 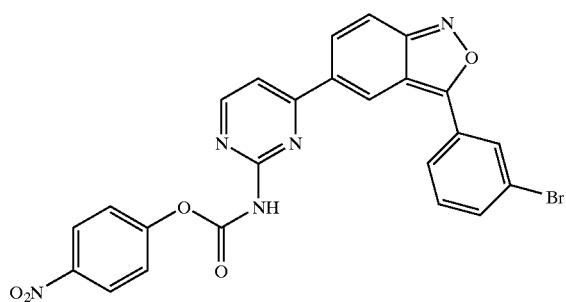 |

TABLE 1-continued
Examples of Compounds of formula I-A
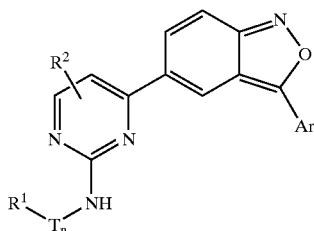
| No. | Structure |
|---|---|
| I-A68 | 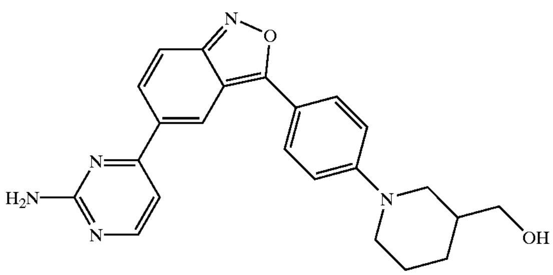 |
| I-A69 | 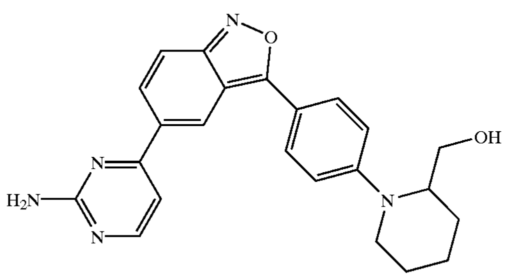 |
| I-A70 | 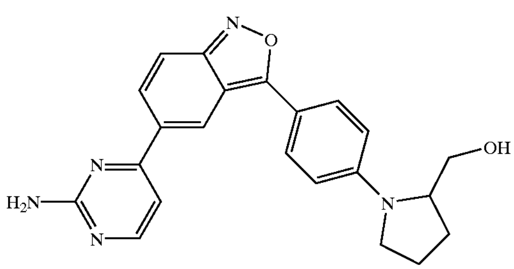 |
| I-A71 | 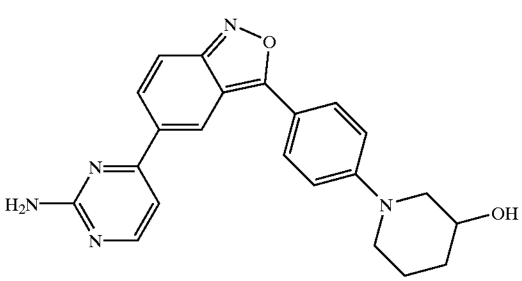 |

TABLE 1-continued
Examples of Compounds of formula I-A
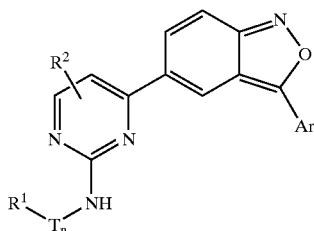
| No. | Structure |
|---|---|
| I-A72 | 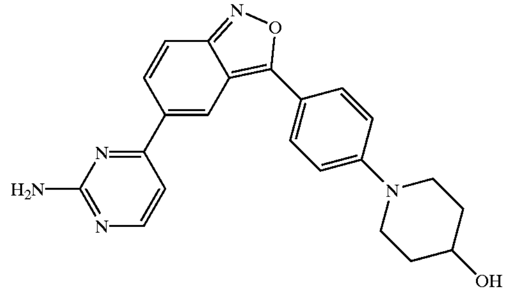 |
| I-A73 | 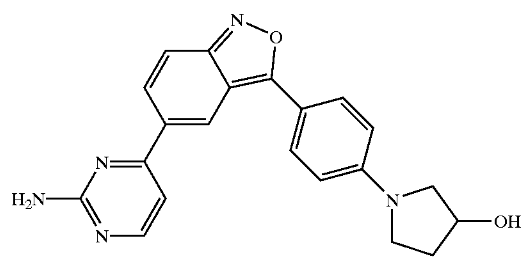 |
| I-A74 | 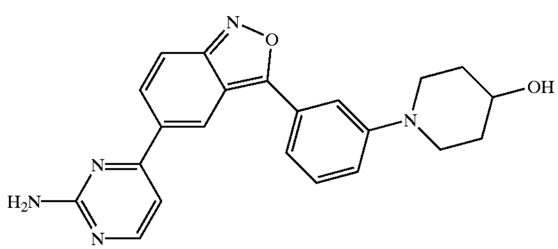 |
| I-A75 | 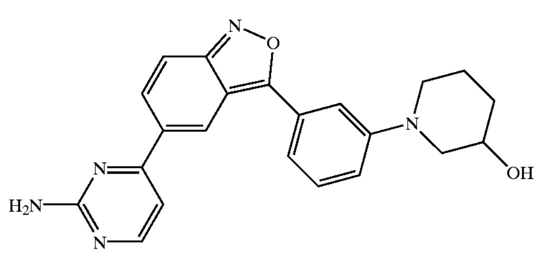 |

TABLE 1-continued
Examples of Compounds of formula I-A
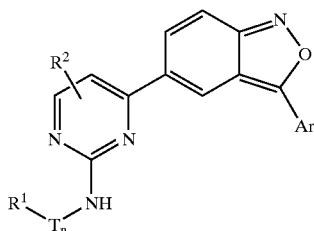
| No. | Structure |
|---|---|
| I-A76 | 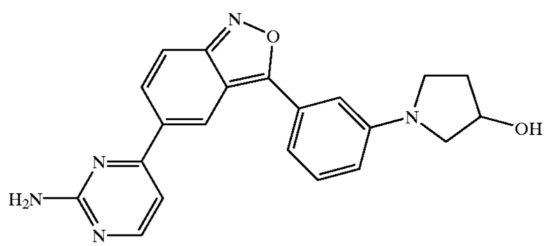 |
| I-A77 | 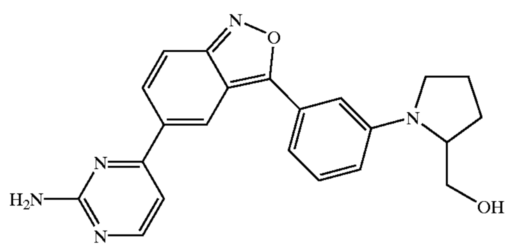 |
| I-A78 | 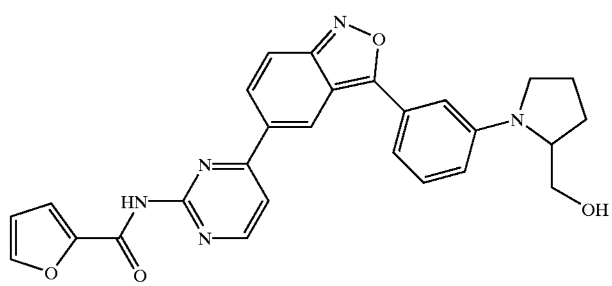 |
| I-A79 | 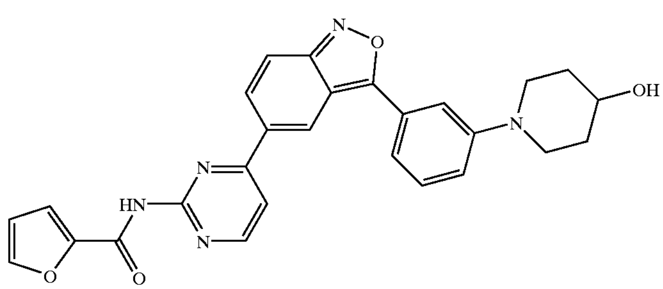 |

TABLE 1-continued
Examples of Compounds of formula I-A
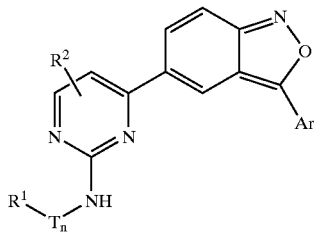
| No. | Structure |
|---|---|
| I-A80 | 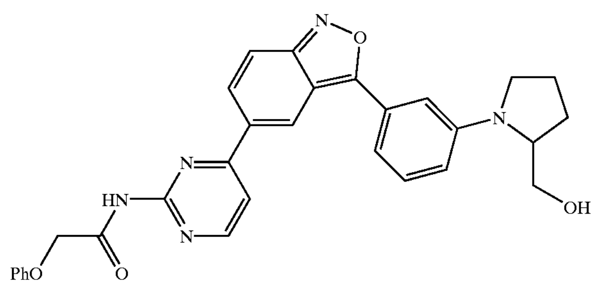 |
| I-A81 | 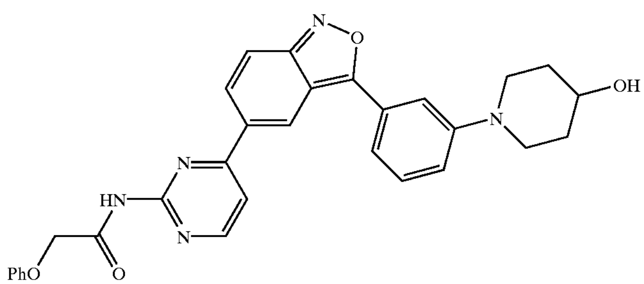 |
| I-A82 | 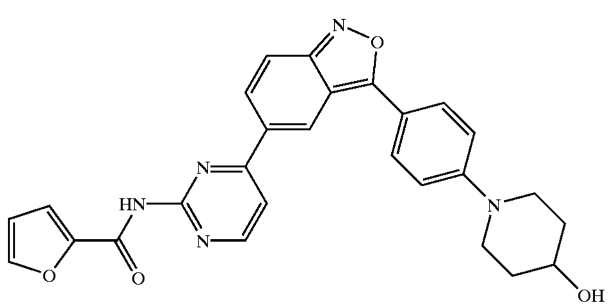 |
| I-A83 | 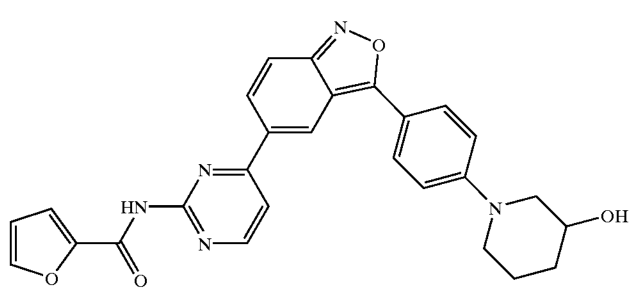 |

TABLE 1-continued
Examples of Compounds of formula I-A
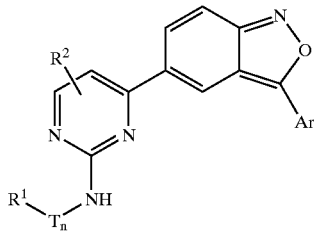
| No. | Structure |
|---|---|
| I-A84 | 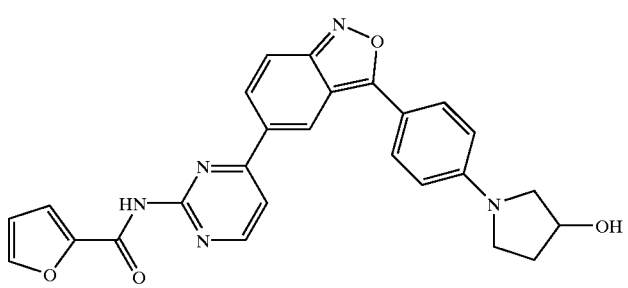 |
| I-A85 | 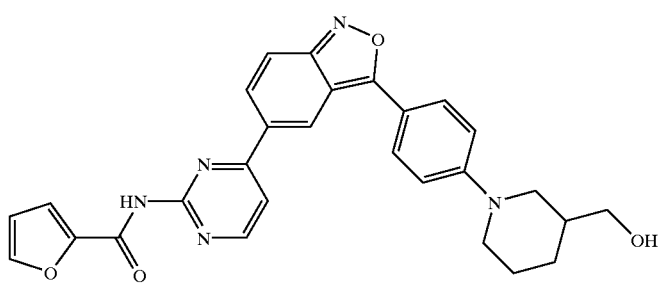 |
| I-A86 | 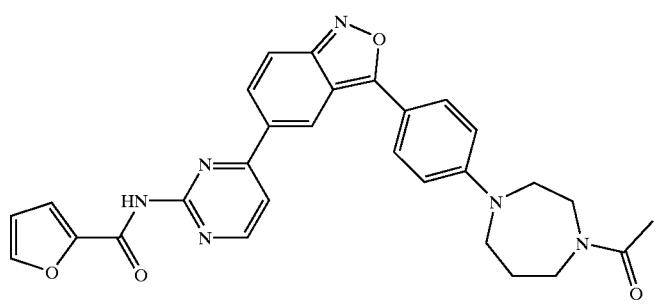 |
| I-A87 | 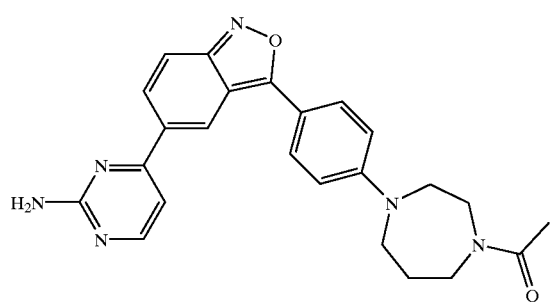 |

TABLE 1-continued
Examples of Compounds of formula I-A
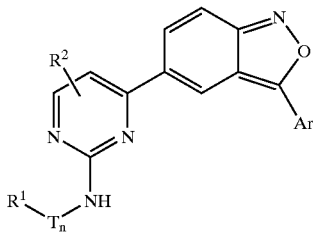
| No. | Structure |
|---|---|
| I-A88 | 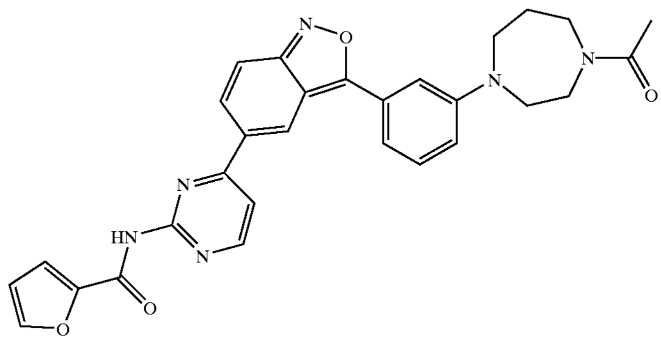 |
| I-A89 | 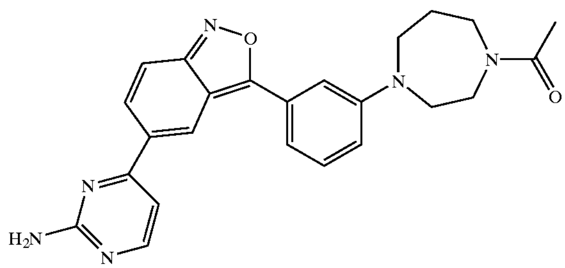 |
The compounds of this invention may be prepared in general by methods known to those skilled in the art for analogous compounds, as illustrated by the general scheme below and by the preparative examples that follow.
Scheme I
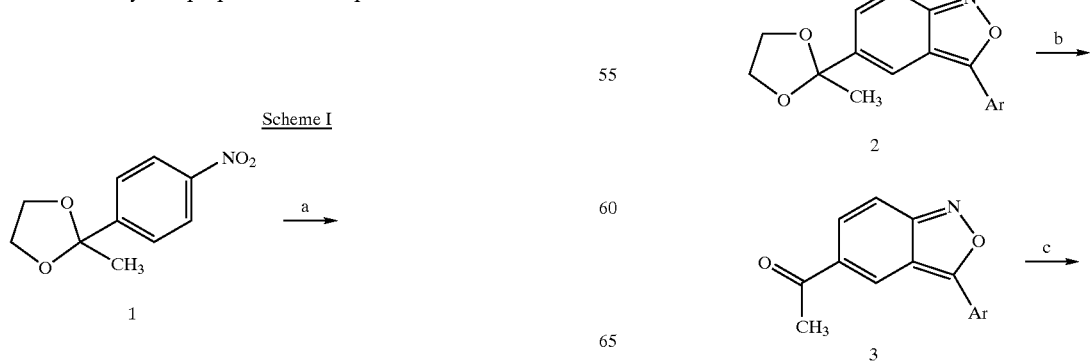

51
-continued

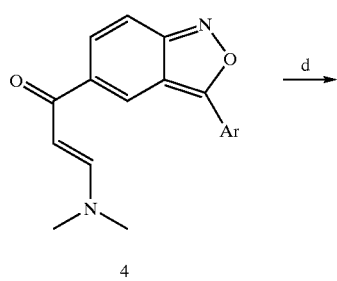

4

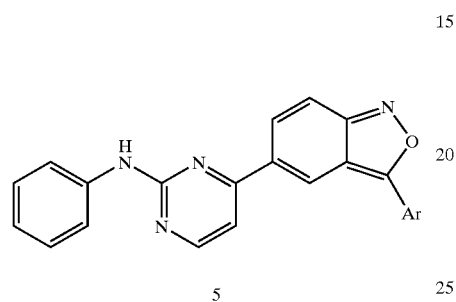

5

Reagents and conditions: (a) ArCH$_2$CN, KOH, MeOH, room temperature (rt);
(b) formic acid, rt (c) N, N-dimethylformamide dimethyl acetal, CH$_3$CN, 80° C.;
(d) N-phenylguanidine-HCl, CH$_3$CN, reflux.

Scheme I above shows a synthetic route for preparing compounds of the present invention. For various Ar groups, the intermediate 3 can be obtained commercially or obtained by known methods as shown in steps (a) and (b) above. See R. B. Davis and L. C. Pizzini, J. Org. Chem., 1960, 25, 1884–1888. A Mannich reaction provides intermediate 4, which can be treated with phenylguanidine to give the desired compounds 5. It will be obvious to one skilled in the art that phenylguanidine may be replaced with other arylguanidines, which are readily available, to provide other compounds of this invention.

Scheme II

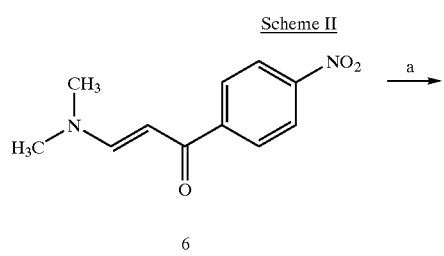

6

52
-continued

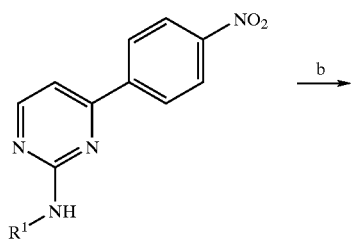

7

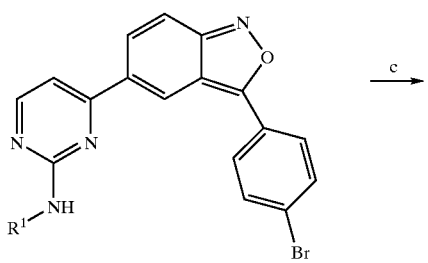

8

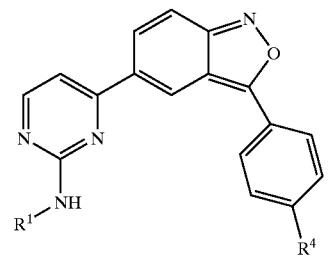

9

Reagents and conditions: (a) R$^1$NHC(=NH)NH$_2$—HCl, CH$_3$CN, reflux; (b) 4-Br—C$_6$H$_4$—CH$_2$CN, KOH, MeOH, room temperature (rt); (c) R$^4$B(OH)$_2$, Pd(PPh$_3$)$_4$, Na$_2$CO$_3$, dioxane Scheme II above shows an alternative synthetic route where the pyrimidine ring is constructed before the benzisoxazole ring. Steps (a) and (b) are analogous to the corresponding steps shown above in Scheme I except that they are performed in the opposite order. Step (c) illustrates one of many ways known to those skilled in the art in which certain compounds of this invention may be modified to provide further compounds of this invention. For example, the bromo substituent of compound 8 may be replaced by other groups using standard coupling methods. R$^4$ is preferably an aryl or heteroaryl ring. It will be obvious to one skilled in the art that this scheme may be modified to provide other compounds of this invention.

Scheme III

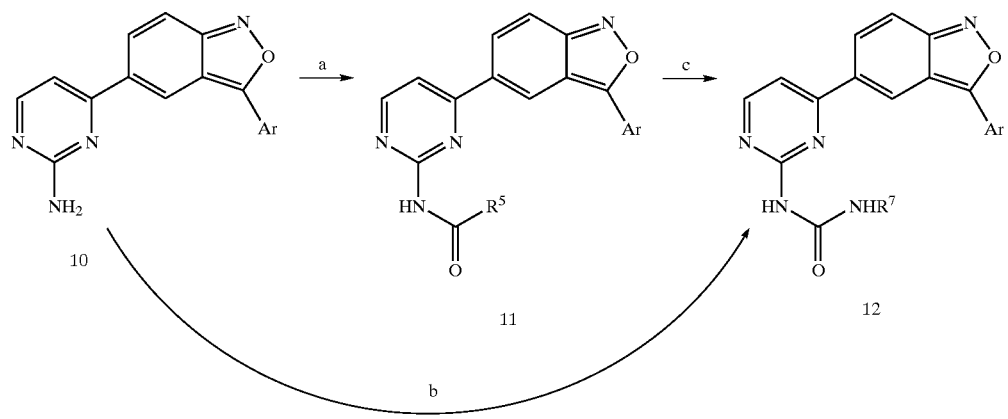

Reagents and conditions: (a) NaH, DMF/THF 1:1, R⁵C(O)Cl, ambient temp; wherein R¹ is —C(O)R⁵;
(b) R⁷NCO, DMSO, ambient temp/80° C.; wherein R¹ is —C(O)NHR⁷; (c) [from the p—NO₂—phenyl carbamic esters] R⁷NH₂, DMSO/THF 1:1, 80° C.; wherein R¹ is —C(O)NHR⁷.
Alternatively, reagents and conditions for carbamate formation (not shown): (a) R⁶OC(O)Cl, DMSO, DIPEA, ambient temp; wherein R¹ is —C(O)OR⁶.

Scheme III shows general methods for the preparation of compounds of Formula I wherein NH—R¹ taken together form an amide (shown in step (a) above), carbamate (not shown) or a urea (shown in steps (a) and (c) or step (b) above). Acylation of the aminopyrimidine with acid chlorides, chloroformates and isocyanates provides amides, cabamates and ureas respectively. Alternatively, ureas can be generated by a nucleophilic displacement reaction with a primary or secondary amine via the corresponding p-nitrophenylcarbamate.

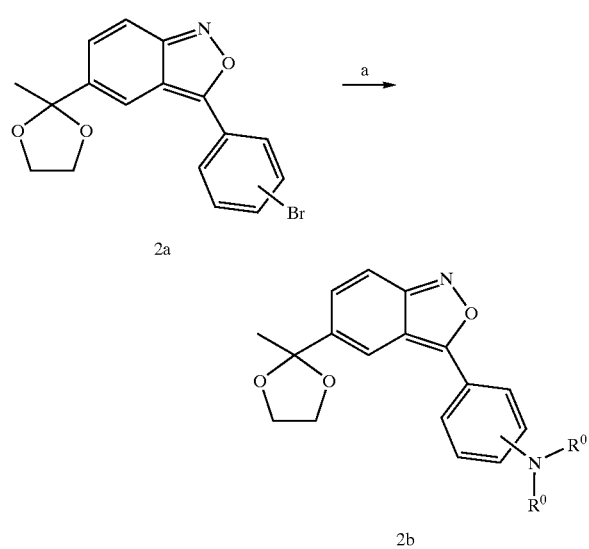

Scheme IV

Reagents and conditions: a) NHR*₂, Pd(OAc)₂,
P—tBu₃, KOtBu, toluene, 90° C.

Scheme IV shows a general method for obtaining compounds 2 (scheme I) wherein the Ar group is substituted with an amine functionality as in 2b, and wherein R* is as described above. Compounds of type 2b may then be taken forward according to Schemes I–II.

The activity of a compound utilized in this invention as an inhibitor of GSK-3 or JAK kinase may be assayed in vitro, in vivo or in a cell line according to methods known in the art. In vitro assays include assays that determine inhibition of either the phosphorylation activity or ATPase activity of activated GSK-3 or JAK. Alternate in vitro assays quantitate the ability of the inhibitor to bind to GSK-3 or JAK. Inhibitor binding may be measured by radiolabelling the inhibitor prior to binding, isolating the inhibitor/GSK-3 or inhibitor/JAK complex and determining the amount of radiolabel bound. Alternatively, inhibitor binding may be determined by running a competition experiment where new inhibitors are incubated with GSK-3 or JAK bound to known radioligands. Detailed conditions for assaying a compound utilized in this invention as an inhibitor of GSK-3 or JAK kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly GSK-3 or JAK kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in GSK-3 or JAK activity between a sample comprising said composition and a GSK-3 or JAK kinase and an equivalent sample comprising GSK-3 or JAK kinase in the absence of said composition.

As used herein, the term "JAK" is used interchangeably with the terms "JAK kinase" and "a JAK family kinase". Preferably JAK refers to JAK3 kinase.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a GSK-3 or JAK family kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride.

Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to about 100% of the amount normally present in a composition comprising that agent as the only therapeutically active agent.

According to another embodiment, the invention relates to a method of inhibiting GSK-3 or JAK kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of GSK-3 or JAK kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of a GSK-3-mediated disease or condition in a patient comprising the step of administering to said patient a composition according to the present invention.

The term "GSK-3-mediated condition", as used herein means any disease or other deleterious condition in which GSK-3, is known to play a role. Such diseases or conditions include, without limitation, diabetes, Alzheimer's disease, Huntington's, Parkinson's, AIDS associated dementia, amyotrophic lateral sclerosis (AML), multiple sclerosis (MS), schizophrenia, cardiomycete hypertrophy, ischemia/reperfusion and baldness.

According to another embodiment, the invention provides a method for treating or lessening the severity of a JAK-mediated disease or condition in a patient comprising the step of administering to said patient a composition according to the present invention.

The term "JAK-mediated disease", as used herein means any disease or other deleterious condition in which a JAK family kinase, in particular JAK3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

Example 1

N-phenylguanidine

Aniline (30 mmol, 1 equiv.), cyanamide (1.3 g, 31 mmol, 1.03 equiv.), and 4N hydrogen chloride in dioxane (8 mL, 32 mmol) was stirred for 10 minutes at room temperature and heated to 80° C. for 18 hours. The mixture was diluted with water (30 mL) and diethyl ether (50 mL). The aqueous layer was washed with ether (30 mL) and the organic layers were discarded. The aqueous layer was neutralized with 6N aqueous HCl (6 mL) and diluted with ethyl acetate (50 mL). The aqueous layer was extracted with ethyl acetate (50 mL) four times. The combined organic layers were concentrated under reduced pressure to afford a solid compound. The solid was washed with diethyl ether (30 mL) to provide pale yellow title compound. The compound was characterized by LC/MS and HPLC.

The following arylguanidine intermediates were prepared by the procedure described above in Example 1 except the aniline was replaced with the appropriate arylamine: N-(4-fluoro-phenyl)-guanidine; N-(6-chloro-pyridin-3-yl)-guanidine; N-(3-chloro-phenyl)-guanidine; N-(3-methoxy-phenyl)-guanidine; N-(3-benzyloxy-phenyl)-guanidine; 4-guanidino-benzenesulfonamide; 3-guanidino-benzenesulfonamide.

The following synthetic intermediates were obtained commercially (from Bionet): 1-[3-phenyl-benzo[c]isoxazol-5-yl]-ethanone; 1-[3-(4-fluoro-phenyl)-benzo[c]isoxazol-5-yl]-ethanone; 1-[3-(4-chloro-phenyl)-benzo[c]isoxazol-5-yl]-ethanone; 3-dimethylamino-1-(3-phenyl-benzo[c]isoxazol-5-yl)-propenone; 3-dimethylamino-1-[3-(4-fluoro-phenyl)-benzo[c]isoxazol-5-yl]-propenone; 3-dimethylamino-1-[3-(4-chloro-phenyl)-benzo[c]isoxazol-5-yl]-propenone; and 1-(4-nitro-phenyl)-3-dimethylamino-propenone.

Example 2

Phenyl-[4-(3-phenyl-benzo[c]isoxazol-5-yl)-pyrimidin-2-yl]-amine (Compound I-A1)

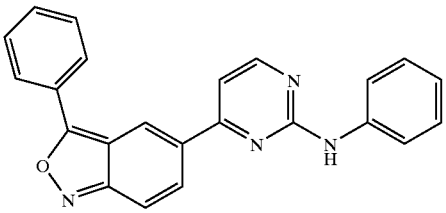

3-Dimethylamino-1-(5-methyl-3-methylsulfanyl-1-phenyl-1H-pyrazol-4-yl)-propenone (30 mg, 0.1 mmol) and N-phenylguanidine (15 mg, 1.1 equiv.) were slurried in acetonitrile (0.5 mL) and heated at 100° C. for 24 hours. The mixture was diluted with methanol (2 mL) and heated briefly and cooled. The resulting solid was filtered and washed with methanol (1 mL). The solid was dried under reduced pressure to afford the title compound. The compound was characterized by LC/MS and HPLC.

Example 3

(4-Fluoro-phenyl)-[4-(3-phenyl-benzo[c]isoxazol-5-yl)-pyrimidin-2-yl]-amine (Compound I-A2)

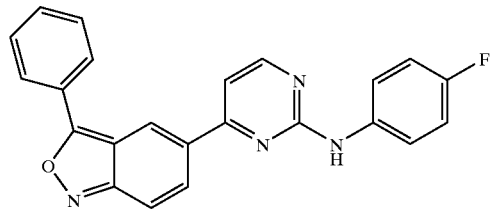

Compound I-A2 was prepared according to the procedure described above in Example 2 except that N-phenylguanidine was replaced by N-(4-fluoro-phenyl)-guanidine.

Example 4

(6-Chloro-pyridin-3-yl)-[4-(3-phenyl-benzo[c]isoxazol-5-yl)-pyrimidin-2-yl]-amine (Compound I-A3)

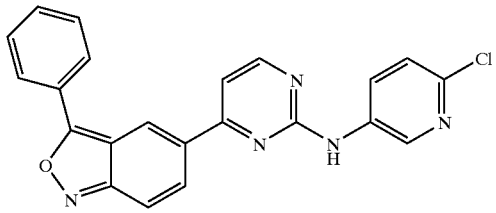

Compound I-A3 was prepared according to the procedure described above in Example 2 except that N-phenylguanidine was replaced by N-(6-chloro-pyridin-3-yl)-guanidine.

Example 5

(3-Chloro-phenyl)-[4-(3-phenyl-benzo[c]isoxazol-5-yl)-pyrimidin-2-yl]-amine (Compound I-A4)

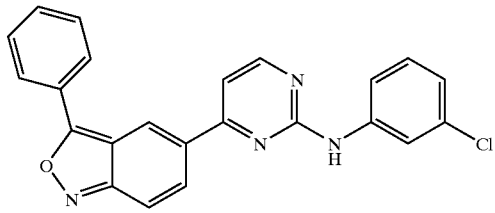

Compound I-A4 was prepared according to the procedure described above in Example 2 except that N-phenylguanidine was replaced by N-(3-chloro-phenyl)-guanidine.

Example 6

4-[4-(3-Phenyl-benzo[c]isoxazol-5-yl)-pyrimidin-2-ylamino]-benzenesulfonamide (Compound I-A19)

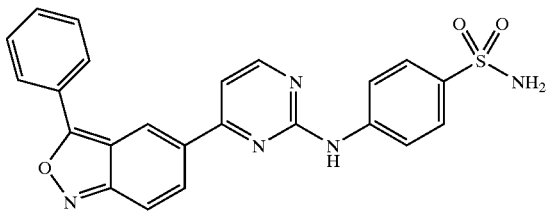

Compound T-A19 was prepared according to the procedure described above in Example 2 except that N-phenylguanidine was replaced by 4-guanidino-benzenesulfonamide.

Example 7

N-{4-[3-(4-Chorophenyl)-benzo[c]isoxazol-5-yl]-pyrimidin-2-yl}-acetamide (1-A22)

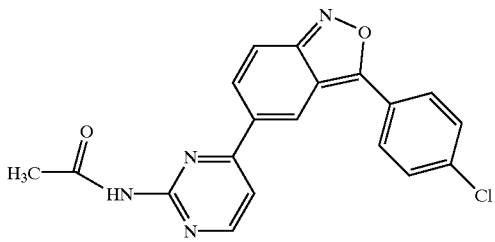

Step A. 4-[3-(4-Chlorophenyl)-benzo[c]isoxazol-5-yl]-pyrimidin-2-ylamine.

To a mixture of sodium pellets (14 mg, 0.609 mmol) in methanol (1 mL) at room temperature, was added guanidine hydrochloride (10 mg, 0.105 mmol) and commercially available 1-[3-(4-chlorophenyl)-benzo[c]isoxazole-5-yl]-3-dimethylamino-propenone (50 mg, 0.153 mmol). The reaction mixture was heated at 80° C. for 18 hours. The mixture was cooled to room temperature and diluted with water (6 mL). The granular precipitate was filtered, dissolved in dichloromethane, then dried over magnesium sulfate. Purification by silica gel chromatography (4:1 ethyl acetate/hexane) gave 4-[3-(4-chlorophenyl)-benzo[c]isoxazol-5-yl]-pyrimidin-2-ylamine as a yellow solid (35 mg, 98% yield). $^1$H NMR (500 MHz, $d_6$-DMSO) δ 8.68 (s, 1H), 8.35 (d, 1H), 8.25–8.19 (m, 3H), 7.82–7.80 (m, 1H), 7.78–7.72 (m, 2H), 7.4 (d, 1H), 6.79 (s, 1H) ppm. LC-MS (ES+) m/e=323.04 (M+H).

Step B. N-{4-[3-(4-Chorophenyl)-benzo[c]isoxazol-5-yl]-pyrimidin-2-yl}-acetamide.

To a suspension of 4-[3-(4-chlorophenyl)-benzo[c]isoxazol-5-yl]-pyrimidin-2-ylamine in toluene (1.5 mL) at room temperature, was added acetic anhydride (0.5 mL). The mixture was heated at 100° C. for 3 hours. The reaction mixture was diluted with water (6 mL) and the precipitate filtered then washed with toluene (2×6 mL). Purification was achieved by silica gel chromatography (4:1 ethyl acetate/hexane then 2% methanol/dichloromethane), followed by a 5% aqueous sodium bicarbonate wash (1×50 mL) to give the title compound as a yellow solid (12 mg, 30% yield). $^1$H NMR (500 MHz, $d_6$-DMSO) δ 10.62 (s, 1H), 8.85 (s, 1H), 8.75 (d, 1H), 8.31 (d, 1H), 8.25 (d, 2H), 8.02 (d, 1H), 7.85 (d, 1H), 7.75 (d, 2H), 2.3 (s, 3H) ppm. LC-MS (ES+) m/e=365.13 (M+H).

Example 8

{4-[3-(4-Chlorophenyl)-benzo[c]isoxazol-5-yl]-pyrimidin-2-yl}-methylamine (1-A23)

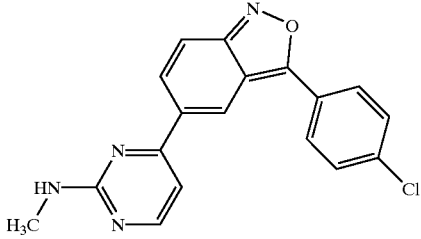

This compound was prepared in an analogous manner to that described in Example 2 using 1-methylguanidine hydrochloride to yield the title compound as a yellow solid (30 mg, 98% yield). $^1$H NMR (500 MHz, $d_6$-DMSO) δ 8.7 (s, 1H) 8.41 (s, 1H), 8.31–8.2 (m, 3H), 7.82 (d, 1H), 7.72 (d, 2H), 7.38 (d, 1H), 7.25–7.2 (m, 1H), 2.95–2.85 (m, 3H) ppm. LC-MS (ES+) m/e=337.04 (M+H).

Example 9

3-(4-Chlorophenyl)-5-(2-morpholin-4-yl-pyrimidin-4-yl)-benzo[c]isoxazole (1-A24)

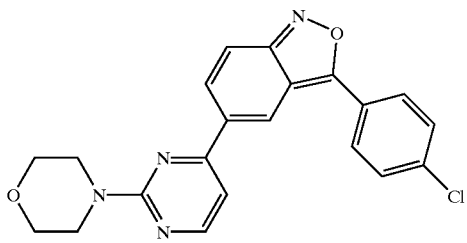

This compound was prepared according to the procedure described in Example 13, Step E, except using morpholinoformamidine hydrobromide to yield 3-(4-chlorophenyl)-5-(2-morpholin-4-yl-pyrimidin-4-yl)-benzo[c]isoxazole as a yellow solid (30 mg, 98% yield). $^1$H NMR (500 MHz, d$_6$-DMSO) δ 8.7 (S, 1H), 8.5 (d, 1H), 8.3–8.22 (m, 3H), 7.82 (s, 1H), 7.75 (d, 2H), 7.55 (d, 1H), 3.85–3.8 (m, 4H), 3.75–3.68 (m, 4H) ppm. LC-MS (ES+) m/e=393.13 (M+H).

Example 10

4-[3-(4-Piperidin-1-yl-phenyl)-benzo[c]isoxazol-5-yl]pyrimidin-2-ylamine (1-A32)

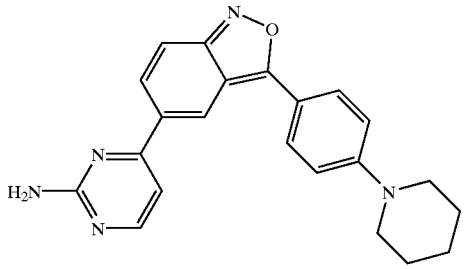

Step A. 5-(2-Methyl-[1,3]dioxolan-2-yl)-3-(4-piperidin-1-yl-phenyl)benzo[c]isoxazole This compound was prepared in a manner analogous to that described in Example 13, Step B except starting with piperidine and a reaction duration of 2.5 h, giving the title compound, after purification, as a bright yellow solid (174 mg, 69% yield). $^1$H NMR (500 MHz, CDCl$_3$) δ 8.02–7.81 (m, 3H), 7.53 (d, J=9.25 Hz, 1H), 7.10–6.92 (m, 2H), 4.15–3.96 (m, 2H), 3.94–3.71 (m, 2H), 3.47–3.23 (m, 4H), 1.83–1.60 (m, 9H). LC-MS (ES+) m/e=365.19 (M+H).

Step B. 1-[3-(4-Piperidin-1-yl-phenyl)-benzo[c]isoxazol-5-yl)ethanone

This compound was prepared in a manner analogous to that described in Experiment 17, Step C giving the title compound as an orange oil (42.6 mg, 97% yield). $^1$H NMR (500 MHz, CDCl$_3$) δ 8.57–8.47 (m, 1H), 8.01–7.91 (m, 2H), 7.88 (dd, J=1.5, 9.4 Hz, 1H), 7.55 (dd, 0.85, 9.4 Hz, 1H), 7.08–6.94 (m, 2H), 3.46–3.30 (m, 4H), 2.66 (s, 3H), 1.82–1.59 (m, 6H). LC-MS (ES+) m/e=321.1 (M+H).

Step C. 4-[3-(4-Piperidin-1-yl-phenyl)-benzo[c]isoxazol-5-yl]pyrimidin-2-ylamine (1-A32)

This compound was prepared in a manner analogous to that described in Experiment 17, Steps D & E giving the title compound as an orange solid (30 mg, 70% yield from 1-[3-(4-piperidin-1-yl-phenyl)-benzo[c]isoxazol-5-yl) ethanone). $^1$H NMR (500 MHz, CDCl$_3$) δ 8.58 (s, 1H), 8.38 (d, J=5.25 Hz, 1H), 8.06–7.85 (m, 3H), 7.62 (d, J=9.4 Hz, 1H), 7.16–6.92 (m, 3H), 5.19–4.91 (br s, 2H), 3.45–3.25 (m, 4H), 1.82–1.61 (m, 6H). HPLC (cyano column) 14.26 min. LC-MS (ES+) m/e=372.2 (M+H).

Example 11

4-[3-(3-Piperidin-1-yl-phenyl)-benzo[c]isoxazol-5-yl]-pyrimidin-2-ylamine (1-A33)

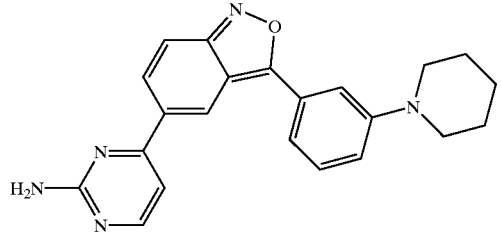

Step A. 3-(3-Bromophenyl)-5-(2-methyl-[1,3]dioxolan-2-yl)benzo[c]isoxazole

To a solution of KOH (58 g, 1.03 mol) in MeOH (200 mL) at room temperature was added a solution of 2-methyl-2-(4-nitro-phenyl)-[1,3]dioxolane (10.79, 0.051 mol) and 3-bromophenylacetonitrile (11.34 g, 0.058 mol) in MeOH (100 mL). The mixture was stirred at room temperature under a stream of nitrogen for 4 days. The product was isolated according to the procedure given in Example 15 Step A (8.5 g, 46% yield). $^1$H NMR (500 MHz, CDCl$_3$) δ 8.19–8.15 (m, 1H), 7.97 (d, 4.0 Hz, 1H), 7.90 (s, 1H), 7.67–7.59 (m, 2H), 7.50–7.40 (m, 2H), 4.15–4.03 (m, 2H), 1.71 (s, 3H). LC-MS ES+) m/e=361.96 (M+H).

Step B. 3-Dimethylamino-1-[3-(3-piperidin-1-yl-phenyl)-benzo[c]isoxazol-5-yl]-propanone This was prepared according to the procedure described in Example 13 to give the title compound as a brown solid (141 mg, 48% yield from 3-(3-bromophenyl)-5-(2-methyl-[1,3] dioxolan-2-yl)benzo[c]isoxazole). $^1$H NMR (500 MHz, DMSO-d$_6$) δ 8.50 (s, 1H), 8.09–7.89 (m, 1H), 7.89–7.64 (m, 2H), 7.63–7.45 (m, 3H), 7.42–7.13 (m, 1H), 6.01 (d, J=12.2 Hz, 1H), 3.51–3.27 (m, 4H), 3.26–3.07 (m, 3H), 3.06–2.80 (m, 3H), 1.84–1.42 (m, 6H). LC-MS ES+) m/e=371.31 (M+H). HPLC (cyano column) 14.13 minutes.

Step C. 4-[3-(3-Piperidin-1-yl-phenyl)-benzo[c]isoxazol-5-yl]-pyrimidin-2-ylamine (1-A33)

This compound was prepared in a manner analogous to that described in Experiment 17, Step E. The title compound was isolated as a yellow/brown solid (97 mg, 69%). $^1$H NMR (500 MHz, CDCl$_3$) δ 8.56 (S, 1H), 8.39 (D, J=5.2 Hz, 1H), 7.97 (dd, J=1.3, 9.4 Hz, 1H), 7.69 (d, 9.5 Hz, 1H), 7.63–7.53 (m, 1H), 7.52–7.37 (m, 2H), 7.17–7.02 (m, 2H), 5.16 (br s, 2H), 3.39–3.19 (m, 4H), 1.86–1.53 (m, 6H). LC-MS ES+) m/e=361.96 (M+H). HPLC (cyano column) 12.01 minutes.

Example 12

4-[4-(4-Nitro-phenyl)-pyrimidin-2-ylamino]-benzenesulfonamide

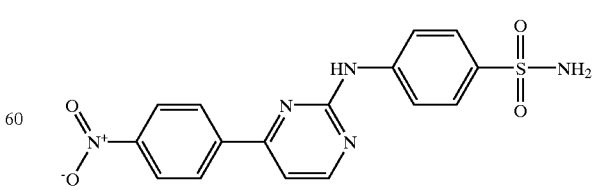

1-(4-Nitro-phenyl)-3-dimethylamino-propenone (3 mmol) and 4-guanidino-benzenesulfonamide (3.3 mmol) in acetonitrile (1 mL) was refluxed for 36 hours. The mixture was diluted with methanol (5 mL) and cooled to room temperature. The yellow solid was filtered and washed with methanol (3 mL) and dried under reduced pressure to afford title compound. The compound was characterized by LC/MS and HPLC.

Example 13

4-[3-(4-Morpholin-4-yl-phenyl)benzo[c]isoxazol-5-yl]pyrimidin-2-yl amine (1-A34)

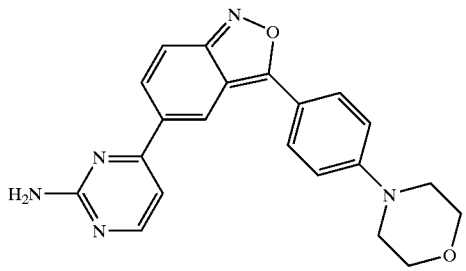

Step A. 3-(4-Bromo-phenyl)-5-(2-methyl-[1,3]-dioxolan-2-yl)-benzo[c]isoxazole

To solution of KOH (28.46 g, 508 mmol) in MeOH (50 mL) at 0–10° C. was added a solution of 4-bromophenylacetonitrile (6.32 g, 32.2 mmol) and 2-methyl-2-(4-nitro-phenyl)-[1,3]-dioxolane (I) (5.35 g, 25.6 mmol) in MeOH (15 mL). The mixture was stirred at room temperature under nitrogen for 18 hours giving a thick slurry. Water (100 mL) was added and the precipitate was filtered, and was washed with water (2×75 mL). The solid was dissolved in hot $CH_2Cl_2$, filtered and evaporated to give a brown solid. Repeated triturations with $Et_2O$ gave the product as a bright orange solid (5.19 g, 56% yield). $^1$H NMR (500 MHz, CDCl$_3$) δ 7.99–7.68 (m, 1H), 7.79–7.68 (m, 2H), 7.66–7.54 (m, 1H), 7.52–7.40 (m, 1H), 4.17–4.04 (m, 2H), 3.92–3.78 (m, 2H), 1.70 (s, 3H) ppm. LC-MS (ES+) m/e=361.9 (M+H).

Step B. 5-(2-Methyl-[1,3]-dioxolan-2-yl)-3-(4-morpholin-4-yl-phenyl)-benzo[c]isoxazole A flame dried, argon flushed flask was charged with 3-(4-bromo-phenyl)-5-(2-methyl-[1,3]-dioxolan-2-yl)-benzo[c]isoxazole (199.6 mg, 0.56 mmol), Pd(OAc)$_2$ (5 mg, 0.02 mmol), P(tBu)$_3$ (30 µL of 10% solution in toluene, 0.012 mmol), NaOtBu (78.8 mg, 0.82 mmol) and morpholine (150 µL, 1.72 mmol) in anhydrous toluene (1 mL). The mixture was heated at 80° C. under Argon for 3 hours. The solvent was evaporated, and purification by flash chromatography (SiO$_2$) eluting initially with 1:9 EtOAc:hexanes to 3:7 EtOAc:hexanes provided the title compound as bright yellow solid (49 mg, 24% yield). $^1$H NMR (500 MHz, CDCl$_3$) δ 7.96 (d, 2H), 7.91 (s, 1H), 7.55 (d, J=9.35 Hz, J=8.9 Hz, 1H), 7.47–7.34 (m, 1H), 7.04 (d, J=8.95 Hz, 2H), 4.17–4.01 (m, 2H), 3.95–3.76 (m, 6H), 3.31 (t, J=5 Hz, 4H), 1.7 (s, 3H). HPLC (cyano column) 8.61 minutes Step C. 1-[3-(4-Morpholin-4-yl-phenyl)benzo[c]isoxazol-5-yl]ethanone A solution of 5-(2-methyl-[1,3]-dioxolan-2-yl)-3-(4-morpholin-4-yl-phenyl)-benzo[c]isoxazole (37 mg, 0.10 mmol) in formic acid (88% solution, 1.5 mL) was stirred at room temperature for 70 minutes. The formic acid was removed in vacuo, and the resultant solid was dissolved in $CH_2Cl_2$, dried over sodium sulfate, filtered and evaporated to give the product as an orange solid (1.42 g, 87% yield). $^1$H NMR (500 MHz, DMSO-d6) δ 8.51 (s, 1H), 7.99 (d, J=8.9 Hz, 2H), 7.88 (d, J=1.0 Hz, 1H), 7.58 (d, 9.4 Hz, 1H), 3.90 (t, J=4.8 Hz, 4H), 3.35 (t, J=5.0 Hz, 4H), 2.66 (s, 3H). LC-MS (ES+) m/e=323.09 (M+H).

Step D. 3-Dimethylamino-1-[3-(4-morpholino-4-yl-phenyl)-benzo[c]isoxazol-5-yl]propenone A solution of 1-[3-(4-morpholin-4-yl-phenyl) benzo[c]isoxazol-5-yl]ethanone (25 mg, 0.08 mmol) in DMF (2.5 mL) was treated with DMF-DMA (50 µL, 0.37 mmol) and was heated at 90° C. for 36 hours and for 100° C. for a further 18 hours. The solvent was evaporated to give the crude product as brown oil (35.2 mg) which was used directly in the next step without purification. LC-MS (ES+) m/e=378.2 (M+H).

Step E. 4-[3-(4-Morpholin-4-yl-phenyl)benzo[c]isoxazol-5-yl]pyrimidin-2-yl amine (I-A34)

To a solution of sodium (spheres, 25 mg, 1.08 mmol) in MeOH (0.7 mL) at room temperature under nitrogen was added guanidine hydrochloride (10 mg, 0.105 mmol) and a solution of 3-dimethylamino-1-[3-(4-morpholino-4-yl-phenyl)-benzo[c]isoxazol-5-yl]propenone (0.08 mmol) in MeOH (1.5 mL) and the reaction was heated to 90° C. for 18 hours. The resulting precipitate was filtered to give the product as an orange solid (25 mg, 84% yield). $^1$H NMR (500 MHz, DMSO-d6) δ 8.61 (s, 1H), 8.33 (d, 1H), 7.98–8.10 (m, 3H), 7.23–6.98 (m, 3H), 3.96–3.75 (m, 4H), 3.43–3.30 (m, 4H), 2.62–2.49 (m, 2H). LC-MS (ES+) m/e= 374.18 (M+H), HPLC (cyano column) 9.42 minutes.

Example 14

4-{4-[3-(3,4-Dimethoxy-phenyl)-benzo[c]isoxazol-5-yl]-pyrimidin-2-ylamino}-benzenesulfonamide (Compound I-A35)

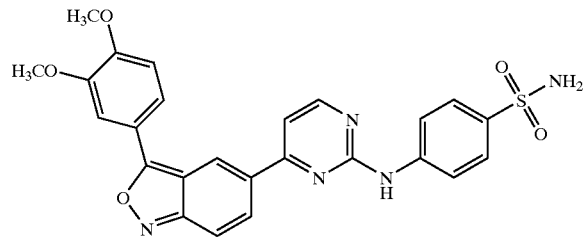

A mixture of 4-[(4-(4-Nitro-phenyl)-pyrimidin-2-ylamino]-benzenesulfonamide (0.2 mmol) and 3,4-dimethoxy-phenylacetonitrile (0.4 mmol) in dimethyl sulfoxide (2 mL) was treated with 20% sodium ethoxide in ethanol (0.5 mL) at ice bath temperature. The mixture was stirred at room temperature for 18 hours and diluted with methanol (2 mL). Solid was collected and redissolved in methanol (3 mL) and heated 10 minutes at 80° C. and cooled to room temperature. The solid was recrystallized twice in methanol to afford yellow title compound. The compound was characterized by LC/MS and HPLC.

Example 15

4-[3-(4-Bromophenyl)-benzo[c]isoxazol-5-yl]-pyrimidin-2-ylamine (1-A36)

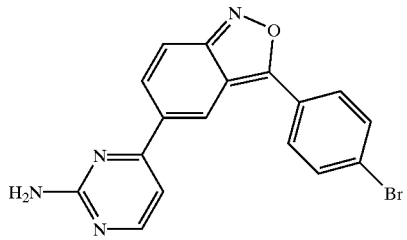

Step A. 1-[3-(4-Bromophenyl)-benzo[c]isoxazol-5-yl]-ethanone

A solution of 3-(4-bromo-phenyl)-5-(2-methyl-[1,3]-dioxolan-2-yl)-benzo[c]isoxazole (Example 1, Step A) (2.13 g, 5.93 mmol) in formic acid (88% solution, 50 ml) was stirred at room temperature for 30 minutes, affording a thick yellow precipitate. The formic acid was removed in vacuo, and the resultant solid was dissolved in $CH_2Cl_2$, dried over sodium sulfate, filtered and evaporated to give the product as an orange solid (1.42 g, 76% yield). $^1$H NMR (500 MHz, $CDCl_3$) δ 8.47 (s, 1H), 8.04–7.85 (m, 3H), 7.85–7.71 (m, 2H), 7.72–7.57 (m, 1H), 2.68 (s, 3H). HPLC (cyano column) 17.68 minutes Step B. 1-[3-(4-Bromo-phenyl)-benzo[c]isoxazol-5-yl]-3-dimethylamino-propenone This compound was prepared from [3-(4-bromophenyl)-benzo[c]isoxazol-5-yl]-ethanone in an analogous manner to Experiment 15, Step D except that the reaction duration was 18 hours. The product was isolated as a brown solid and was used in the next step without purification (1.61 g, 97% yield). $^1$H NMR (500 MHz, $CDCl_3$) d 8.84 (s, 1H), 7.98–7.79 (m, 4H), 7.77–7.67 (m, 2H), 7.66–7.51 (m, 1H), 5.67 (d, J=12.2 Hz, 1H), 3.31–2.78 (m, 6H).

Step C. 4-[3-(4-Bromophenyl)-benzo[c]isoxazol-5-yl]-pyrimidin-2-ylamine

This compound was prepared in an analogous manner to 4-[3-(4-chlorophenyl)-benzo[c]isoxazol-5-yl]-pyrimidin-2-ylamine (see Example 13). Purification was achieved by trituration with dichloromethane to yield 4-[3-(4-bromophenyl)-benzo[c]isoxazol-5-yl]-pyrimidin-2-ylamine as a yellow solid (559 mg, 49% yield). $^1$H NMR (500 MHz, $d_6$-DMSO) δ 8.67 (s, 1H), 8.36 (d, 1H), 8.2–8.13 (m, 3H), 7.88 (d, 2H), 7.82 (d, 1H), 7.39 (d, 1H), 6.78 (s, 1H) ppm. LC-MS (ES+) m/e=367 (M+H).

Example 16

3-[4-(3-Phenyl-benzo[c]isoxazol-5-yl)-pyrimidin-2-ylamino]-benzenesulfonamide (Compound I-A37)

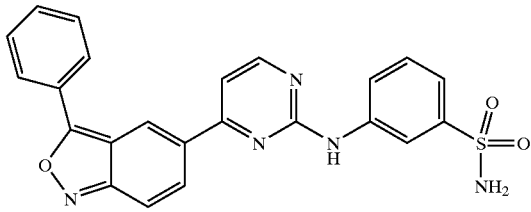

Compound I-A37 was prepared according to the procedure described above in Example 2 except that N-phenylguanidine was replaced by 3-guanidino-benzenesulfonamide.

Example 17

N-(4-{3-[3-(2,5-Dimethoxy-pyrimidin-4-yl)-phenyl]-benzo[c]isoxazol-5-yl}-pyrimidin-2-yl)-acetamide (Compound I-A50).

Step A: N-{4-[3-(3-Bromophenyl)-benzo[c]isoxazol-5-yl]-pyrimidin-2-yl}-acetamide Compound I-A50 was prepared according to the procedure described as above in Example 7 step B utilizing 4-[3-(3-bromophenyl)-benzo[c]isoxazol-5-yl]-pyrimidin-2-ylamine instead of 4-[3-(4-Chlorophenyl)-benzo[c]isoxazol-5-yl]-pyrimidin-2-ylamine. Material was isolated, by removal of the solvent under reduced pressure and trituration with dichloromethane, as a yellow powder (430 mg, 77% yield). $^1$H NMR (500 MHz TFA-d) δ 9.15 (s, 1H), 8.85 (d, 1H), 8.41 (d, 1H), 8.38 (s, 1H), 8.32 (d, 1H), 8.17 (d, 1H), 8.05 (d, 1H), 7.94 (d, 1H), 7.64 (dd, 1H), 2.67 (s, 3H) in ppm. LC-MS (ES+) m/e=409 (M+H).

Step B: N-(4-{3-[3-(2,5-Dimethoxy-pyrimidin-4-yl)-phenyl]-benzo[c]isoxazol-5-yl}-pyrimidin-2-yl)-acetamide A flask was charged with N-{4-[3-(3-bromophenyl)-benzo[c]isoxazol-5-yl]-pyrimidin-2-yl}-acetamide (100 mg, 0.272 mmol), cesium carbonate (97.7 mg, 0.328 mmol), and 2,5-dimethoxypyrimidine-6-boronic acid (55.0 mg, 0.3 mmol). The flask was evacuated and back-filled with nitrogen 5–7 times before adding 5 mL of degassed p-dioxane and 1 mL of degassed DMF. To this stirring solution/suspension was added, 125 μL of a 10% w/v benzene solution of tri-tertbutylphosphine followed by the addition of $Pd_2(dba)_3$ (25 mg, 0.0272 mmol) slurred in 1 mL of degassed DMF. The reaction was stirred under nitrogen atmosphere, at 80° C. Reaction was followed by HPLC and deemed to be complete in 4 hours. The reaction mixture was suction filtered hot through a pad of diatomaceous earth and washed the precipitate with DMF and acetonitrile. The filtrate was reduced to an oil under reduced pressure and the crude material purified via HPLC utilizing acetonitrile/water/TFA as the eluent. The material was isolated as a bright yellow powder (15 mg, 13% yield). $^1$H NMR (500 MHz DMSO-d6) δ 8.93 (s, 1H) 8.6 (s, 1H), 8.31 (s, 1H), 8.29 (d, 1H), 8.25 (d, 1H), 8.07 (d, 1H), 7.87 (d, 1H), 7.81 (d, 1H), 7.77 (m, 1H), 4.02 (2 close sing, 6H) in ppm. LC-MS (ES+) m/e=469 (M+H)

Example 18

{4-[3-(3-Bromo-phenyl)-benzo[c]isoxazol-5-yl]-pyrimidin-2-yl}-carbamic acid ethyl ester (Compound I-A55)

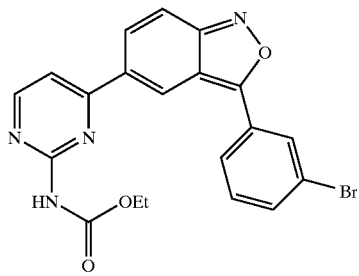

To a stirring solution of 4-[3-(3-bromophenyl)-benzo[c]isoxazol-5-yl]-pyrimidin-2-ylamine (75 mg; 0.205 mmol) in 1 mL of p-dioxane and 0.5 mL of DMSO, was added 40 µL (45.6 mg, 0.42 mmol) of ethyl chloroformate followed by 73 µL (54.3 mg, 0.42 mmol) of diisopropylethylamine. The reaction was stirred at 50° C., in a sealed vessel, for 8 hours. The solvents were removed under vacuo and the crude material was purified via HPLC with acetonitrile/water/TFA as the eluent. The material was isolated as a yellow powder (30 mg, 32% yield). $^1$H NMR (500 MHz, DMSO-d6) δ 10.5 (br s,1H), 8.9 (s, 1H), 8.75 (d, 1H), 8.35 (m, 3H), 8.3(s, 1H), 8.0 (d, 1H), 7.89 (t, 2H), 7.65 (t, 1H), 4.2 (q, 2H), 1.26 (t, 3H) in ppm. LC-MS (ES+) m/e=439/441 (M+H)

Example 19

Thiophene-2-carboxylic acid {4-[3-(3-bromo-phenyl)-benzo[c]isoxazol-5-yl]-pyrimidin-2-yl}-amide (Compound I-A 56)

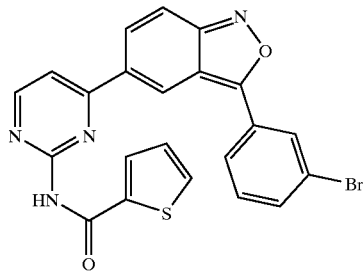

4-[3-(3-bromophenyl)-benzo[c]isoxazol-5-yl]-pyrimidin-2-ylamine (100 mg; 0.272 mmol) was dissolved in 3 mL of a mixture (2:1) of dry DMF/THF and stirred under a nitrogen atmosphere at ambient temperature. Sodium hydride (15 mg, 0.375 mmol, 60% oil dispersion) was added To the reaction and stirred for 30 minutes. Thiophenecarbonylchloride (32 µL; 43.7 mg; 0.299 mmol) in 500 µL of dry DMF was added dropwise over 2 minutes and the reaction was stirred for 18 hours at ambient temperature. Workup was affected by removing the solvents under reduced pressure and the resulting residue was triturated with methyltertbutyl ether. The crude solid was purified via silica column chromatography with 5% ethanol in methylenechloride to yield 32 mg of a tan powder; 24% yield. $^1$H NMR (500 MHz, DMSO-d6) δ 11.2 (s, 1H), 8.92 (s, 1H), 8.88 (d, 1H), 8.39 (d, 1H), 8.35 (s, 1H), 8.3 (d, 1H), 8.23 (d, 1H), 8.15 (d, 1H), 7.95 (d, 1H), 7.9 (d, 1H), 7.87 (d, 1H), 7.65 (t, 1H), 7.24 (t, 1H) in ppm. LC-MS (ES+) m/e=477/479 (M+H).

Biological Methods $IC_{50}$ Determination for the Inhibition of GSK-3

Compounds were screened for their ability to inhibit GSK-3β (Amino Acids 1–420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 10 µM ATP (Sigma Chemicals, St Louis, Mo.) and 300 µM peptide (HSSPHQS($PO_3H_2$)EDEEE, American Peptide, Sunnyvale, Calif.). Reactions were carried out at 30° C. and 60 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. 59 µl of the test reaction was placed in a 96 well ½ diameter plate (Corning, Corning, N.Y.) then treated with 1 µl of a 2 mM DMSO stock containing the test compound (final compound concentration 30 µM). The plate was incubated for about 10 minutes at 30° C. then the reaction initiated by addition of 7 µl of ATP (final concentration 10 µM). Rates of reaction were obtained using a Molecular Devices Spectramax plate reader (Sunnyvale, Calif.) over a 5 minute read time at 30° C. Compounds showing greater than 50% inhibition versus standard wells containing DMSO, but no compound, were titrated and $IC_{50}$ values were determined using a similar protocol in standard 96 well plates with the assay scaled to a final volume of 200 µl.

In the GSK-3 inhibition assay described above, many of the compounds of this invention that were tested were found to provide an $IC_{50}$ value below one micromolar.

$K_i$ Determination for the Inhibition of GSK-3

Compounds were screened for their ability to inhibit GSK-3β (Amino Acids 1–420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (HSSPHQS($PO_3H_2$)EDEEE, American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 µM to 30 µM at 30° C. for 10 minutes. Typically, a 12 point titration was conducted by preparing serial dilutions (from 10 mM compound stocks) with DMSO of the test compounds in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration.

In the GSK-3 inhibition assay described above, many of the compounds of this invention that were tested were found to provide a $K_i$ value below one micromolar.

JAK Inhibition Assay

Compound inhibition of JAK were assayed by the method described by G. R. Brown, et al, *Bioorg. Med. Chem. Lett.* 2000, vol. 10, pp 575–579 in the following manner. Into Maxisorb plates, previously coated at 4° C. with Poly (Glu, Ala, Tyr) 6:3:1 then washed with phosphate buffered saline 0.05% and Tween (PBST), was added 2 μM ATP, 5 mM MgCl$_2$, and a solution of compound in DMSO. The reaction was started with JAK enzyme and the plates incubated for 60 minutes at 30° C. The plates were then washed with PBST, 100 μL HRP-Conjugated 4G10 antibody was added, and the plate incubated for 90 minutes at 30° C. The plate was again washed with PBST, 100 μL TMB solution is added, and the plates were incubated for another 30 minutes at 30° C. Sulfuric acid (100 μL of 1M) was added to stop the reaction and the plate is read at 450 nm to obtain the optical densities for analysis to determine IC$_{50}$ values.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

What is claimed is:

1. A compound of formula I:

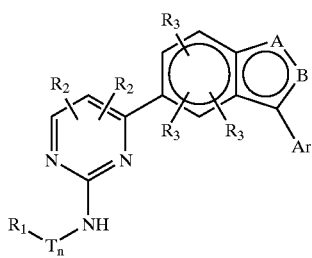

I or a pharmaceutically acceptable salt thereof, wherein:

A-B is N—O or O—N;

Ar is an optionally substituted C$_{5-10}$ aryl group;

T is a C$_{1-4}$ alkylidene chain wherein one or two methylene units of T are optionally and independently replaced by O, NR, S, C(O), C(O)NR, NRC(O)NR, SO$_2$, SO$_2$NR, NRSO$_2$, NRSO$_2$NR, CO$_2$, OC(O), NRCO$_2$, or OC(O)NR;

n is zero or one;

R$^1$ is hydrogen or an optionally substituted group selected from C$_{1-10}$ aliphatic, C$_{5-10}$ aryl, C$_{6-12}$ aralkyl, C$_{3-10}$ heterocyclyl, or C$_{4-12}$ heterocyclylalkyl;

each R$^2$ is independently selected from R, halo, CN, OR, N(R)$_2$, SR, C(=O)R, CO$_2$R, CONR$_2$, NRC(=O)R, NRCO$_2$(C$_{1-6}$ aliphatic), OC(=O)R, SO$_2$R, S(=O)R, SO$_2$NR$_2$, or NRSO$_2$(C$_{1-6}$ aliphatic);

each R$^3$ is independently selected from R, halo, CN, OR, N(R)$_2$, SR, C(=O)R, CO$_2$R, CONR$_2$, NRC(=O)R, NRCO$_2$(C$_{1-6}$ aliphatic), OC(=O)R, SO$_2$R, S(=O)R, SO$_2$NR$_2$, or NRSO$_2$(C$_{1-6}$ aliphatic); and each R is independently selected from hydrogen, a C$_{1-8}$ aliphatic group, or two R on the same nitrogen are taken together with the nitrogen to form a 4–8 membered heterocyclic ring having 1–3 heteroatoms selected from nitrogen, oxygen or sulfur.

2. The compound of claim 1 wherein A-B is N—O.

3. The compounds of claim 2 wherein each R$^2$ is independently hydrogen or a C$_{1-4}$ alkyl group and each R$^3$ is independently selected from hydrogen, halo —O(C$_{1-4}$ alkyl), or C$_{1-4}$ alkyl.

4. The compound of claim 3 wherein Ar is a substituted or unsubstituted five or six-membered aromatic ring having zero to two heteroatoms selected from nitrogen, sulfur, and oxygen.

5. The compound of claim 4 wherein Ar is a substituted or unsubstituted six-membered aromatic ring having zero to two ring nitrogen atoms.

6. The compound of claim 5 wherein Ar is a phenyl ring optionally substituted by one or more substituents independently selected from C$_{1-10}$ aliphatic, C$_{5-10}$ aryl, C$_{6-12}$ aralkyl, C$_{3-10}$ heterocyclyl, C$_{4-12}$ heterocyclylalkyl, halo, CN, OR, N(R)$_2$, SR, C(=O)R, CO$_2$R, CONR$_2$, NRC(=O)R, NRCO$_2$(C$_{1-6}$ aliphatic), OC(=O)R, SO$_2$R, S(=O)R, SO$_2$NR$_2$, or NRSO$_2$(C$_{1-6}$ aliphatic), or two substituents on adjacent positions are optionally taken together with their intervening atoms to form a fused 5–8 membered unsaturated or partially unsaturated ring having zero to two heteroatoms selected from nitrogen, oxygen or sulfur.

7. The compound of claim 6 wherein R$^1$ is a phenyl or pyridyl ring optionally substituted with halogen, —R, —OR, —OH, —SH, —SR, protected OH, —NO$_2$, —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SO$_2$NH$_2$, —S(O)R, —SO$_2$NHR, or —NHS(O)$_2$R, wherein R is an aliphatic group or a substituted aliphatic group having one to three carbons.

8. The compound of claim 7 wherein R$^1$ is substituted by —SO$_2$NH$_2$ or —SO$_2$NHR.

9. The compound of claim 1 wherein the compound is selected from any one of the following:

| No. | Structure |
|---|---|
| I-A1 | 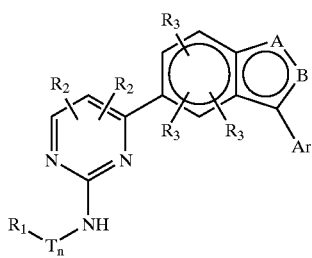 |

-continued
| No. | Structure |
|---|---|
| I-A2 | 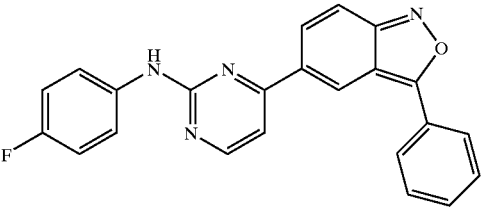 |
| I-A3 | 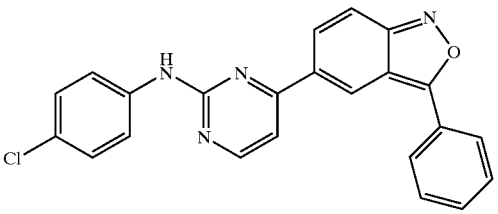 |
| I-A4 | 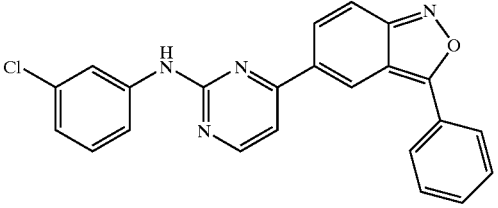 |
| I-A5 | 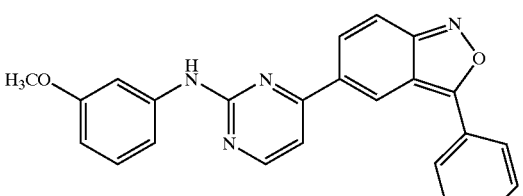 |
| I-A6 | 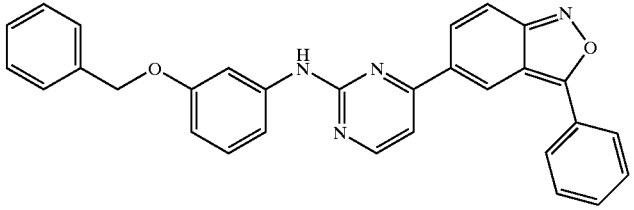 |
| I-A7 | 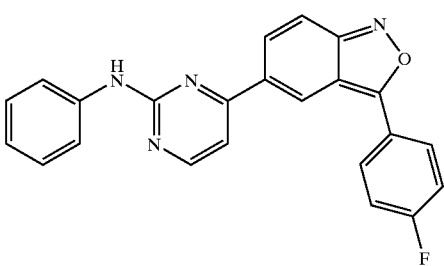 |

-continued
| No. | Structure |
|---|---|
| I-A8 | 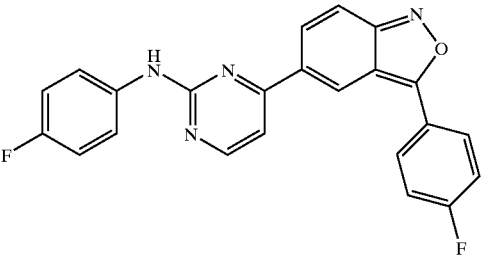 |
| I-A9 | 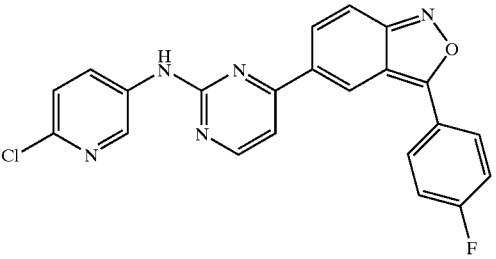 |
| I-A10 | 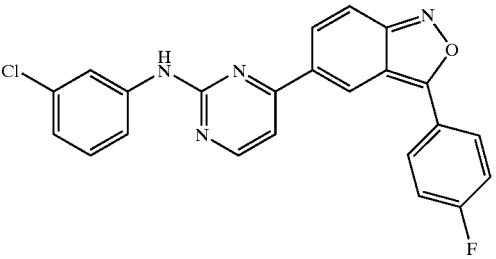 |
| I-A11 | 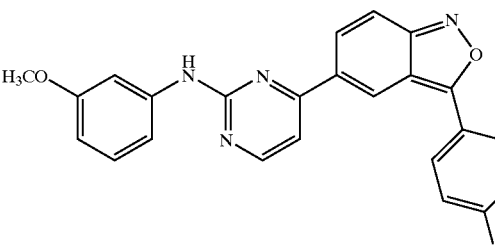 |
| I-A12 | 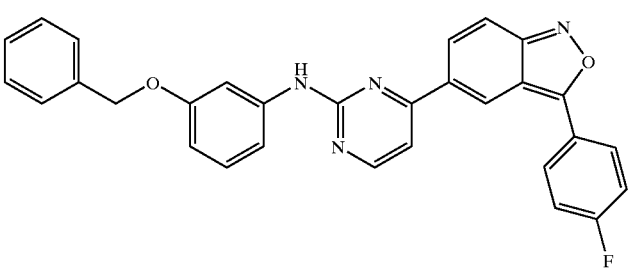 |
| I-A13 | 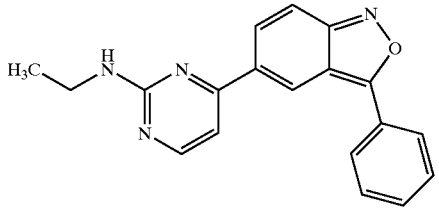 |

-continued
| No. | Structure |
|---|---|
| I-A14 | 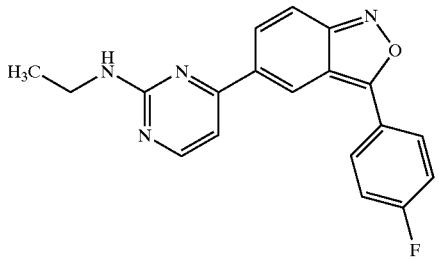 |
| I-A15 | 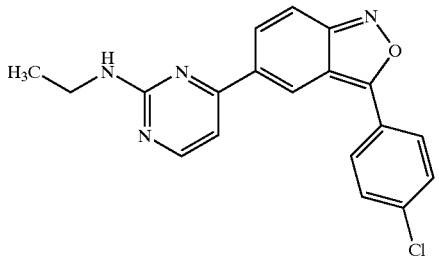 |
| I-A16 | 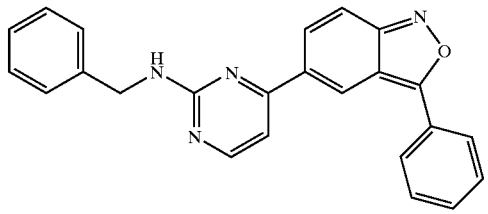 |
| I-A17 | 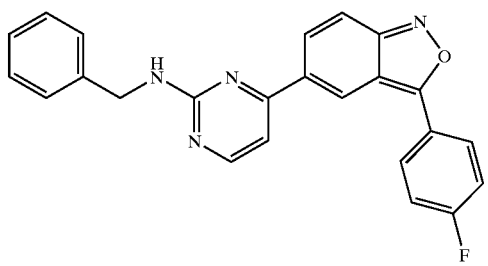 |
| I-A18 | 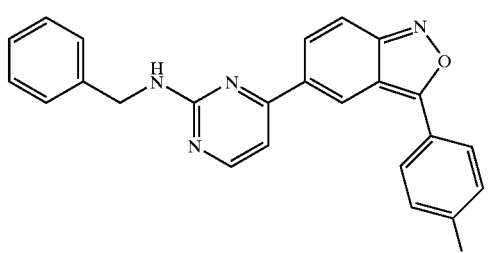 |
| I-A19 | 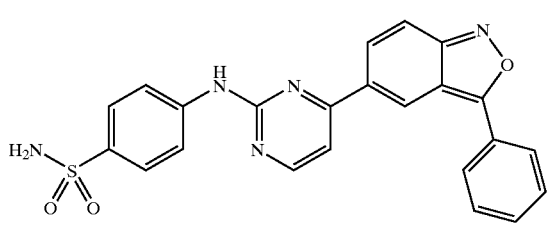 |

-continued

| No. | Structure |
|---|---|
| I-A20 | 4-[[4-[3-(4-fluorophenyl)-2,1-benzisoxazol-5-yl]pyrimidin-2-yl]amino]benzenesulfonamide |
| I-A21 | 4-[[4-[3-(4-chlorophenyl)-2,1-benzisoxazol-5-yl]pyrimidin-2-yl]amino]benzenesulfonamide |
| I-A22 | N-[4-[3-(4-chlorophenyl)-2,1-benzisoxazol-5-yl]pyrimidin-2-yl]acetamide |
| I-A23 | 4-[3-(4-chlorophenyl)-2,1-benzisoxazol-5-yl]-N-methylpyrimidin-2-amine |
| I-A24 | 4-[4-[3-(4-chlorophenyl)-2,1-benzisoxazol-5-yl]pyrimidin-2-yl]morpholine |

-continued

| No. | Structure |
|---|---|
| I-A25 | 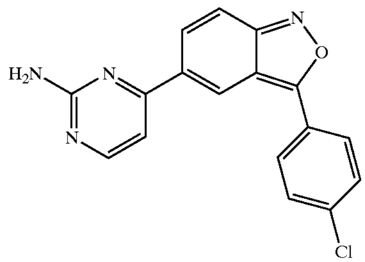 |
| I-A26 | 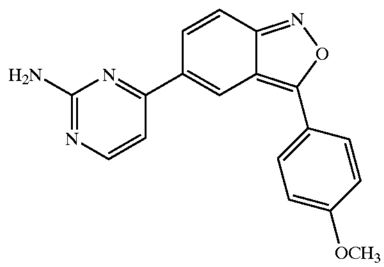 |
| I-A27 | 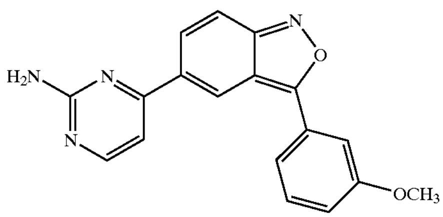 |
| I-A28 | 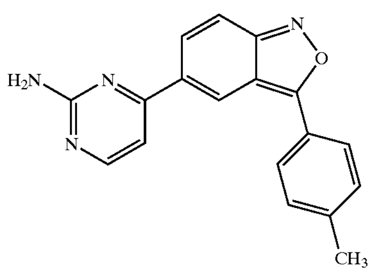 |
| I-A29 | 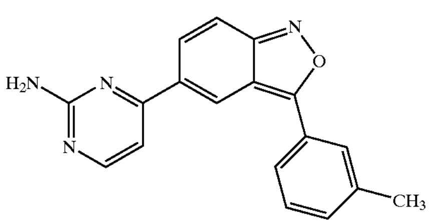 |
| I-A30 | 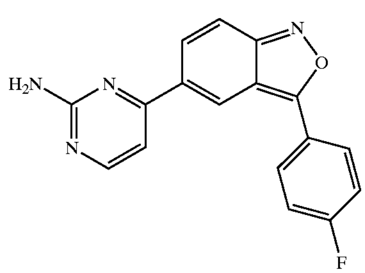 |

| No. | Structure |
|---|---|
| I-A31 | 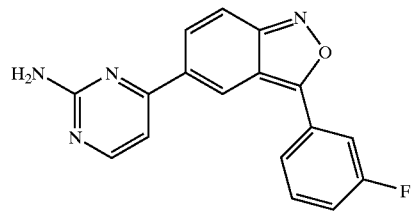 |
| I-A32 | 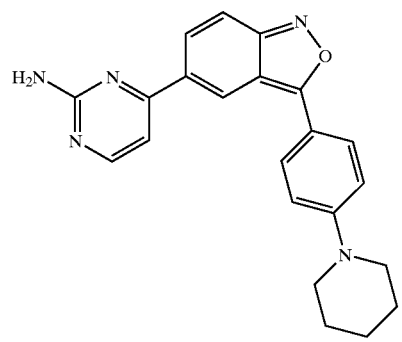 |
| I-A33 | 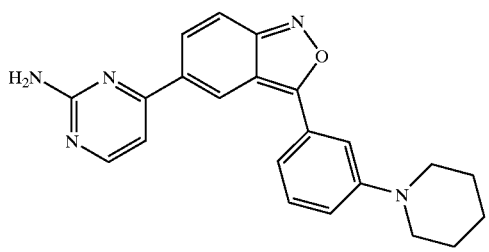 |
| I-A34 | 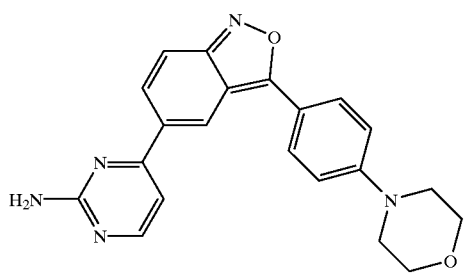 |
| I-A35 | 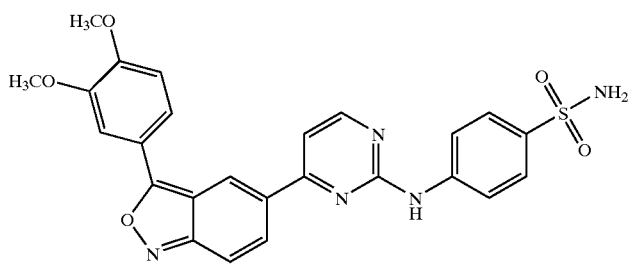 |

-continued
| No. | Structure |
|---|---|
| I-A36 | 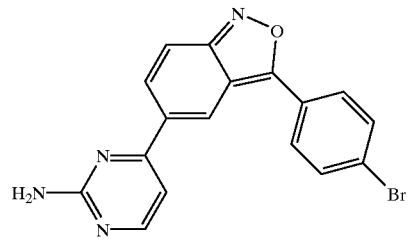 |
| I-A37 | 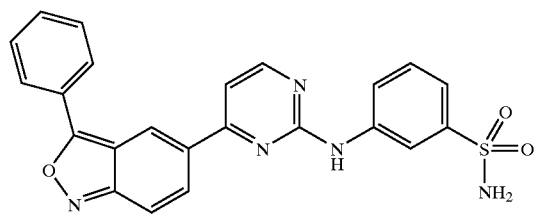 |
| I-A38 | 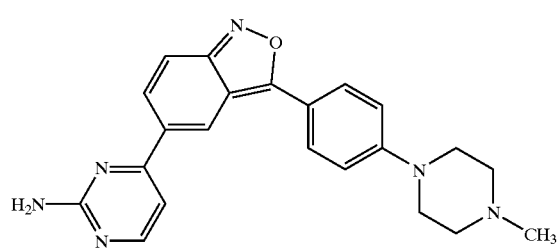 |
| I-A39 | 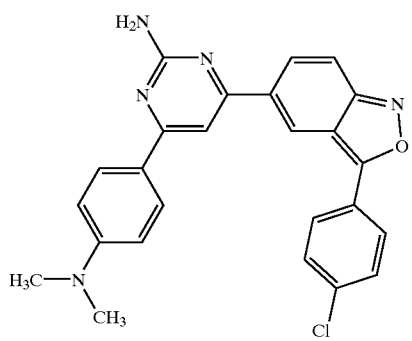 |
| I-A40 | 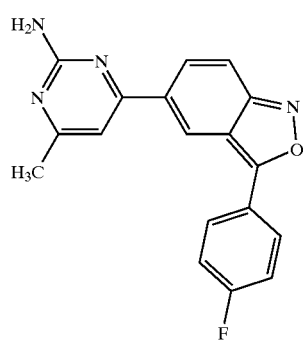 |

-continued
| No. | Structure |
|---|---|
| I-A41 | 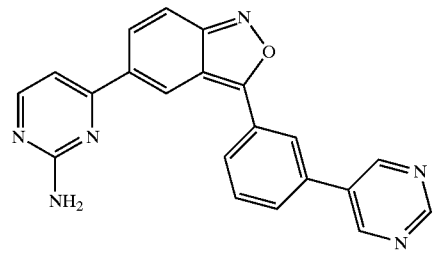 |
| I-A42 | 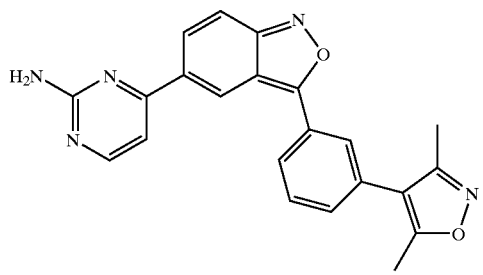 |
| I-A43 | 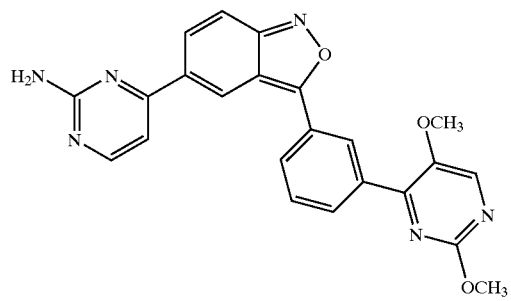 |
| I-A44 | 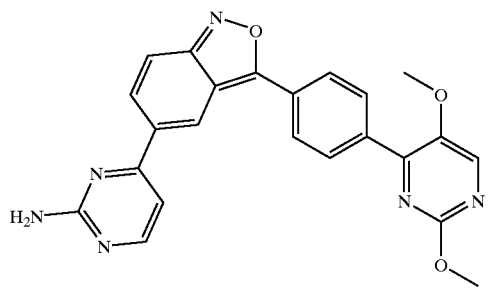 |
| I-A45 | 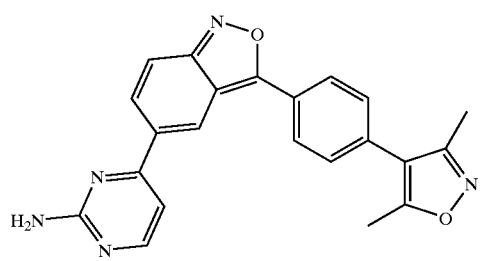 |

-continued
| No. | Structure |
|---|---|
| I-A46 | 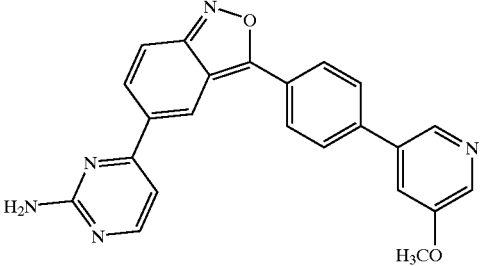 |
| I-A47 | 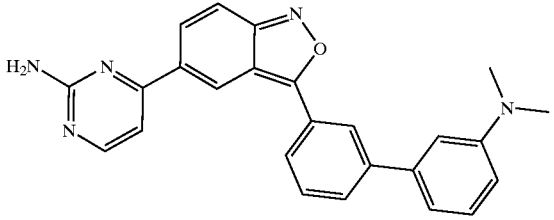 |
| I-A48 | 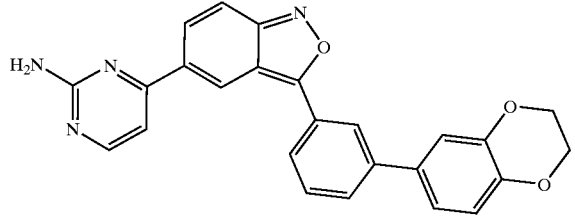 |
| I-A49 | 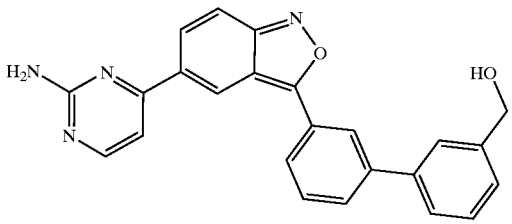 |
| I-A50 | 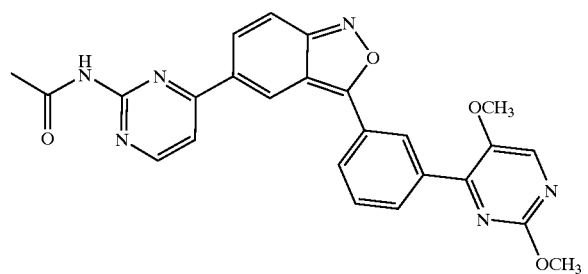 |
| I-A51 | 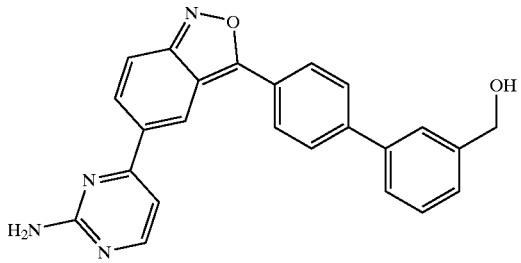 |

-continued
| No. | Structure |
|---|---|
| I-A52 | 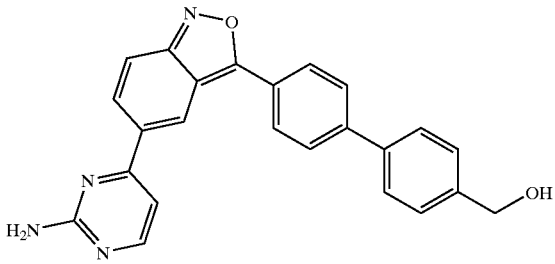 |
| I-A53 | 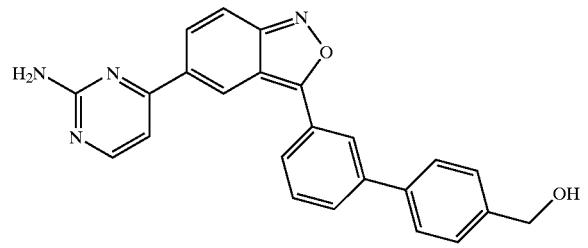 |
| I-A54 | 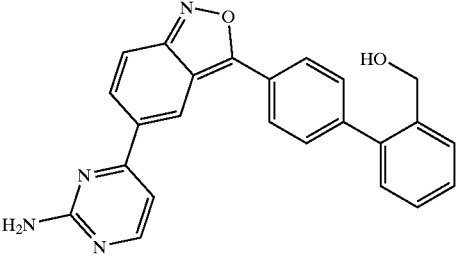 |
| I-A55 | 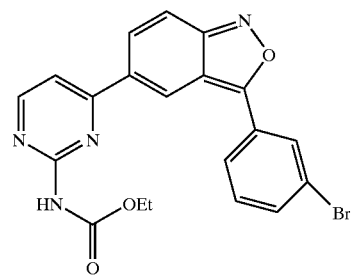 |
| I-A56 | 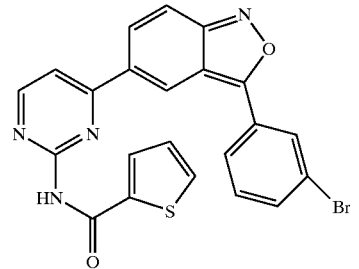 |

-continued

| No. | Structure |
|---|---|
| I-A57 | 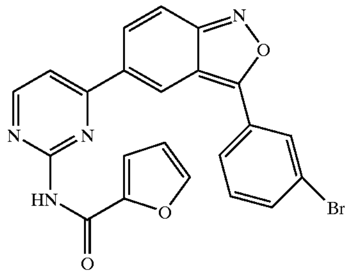 |
| I-A58 | 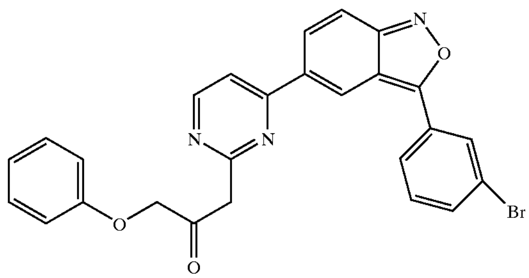 |
| I-A59 | 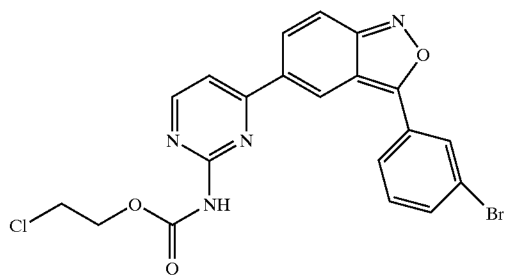 |
| I-A60 | 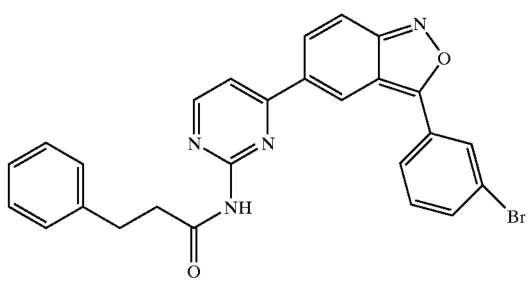 |
| I-A61 | 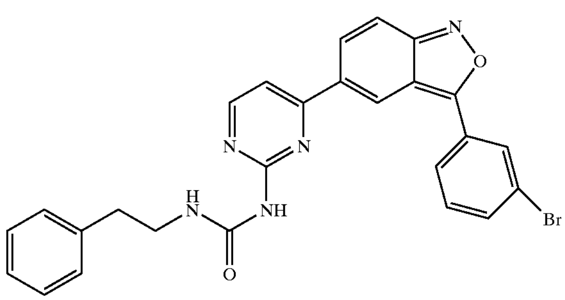 |

-continued

| No. | Structure |
|---|---|
| I-A62 | 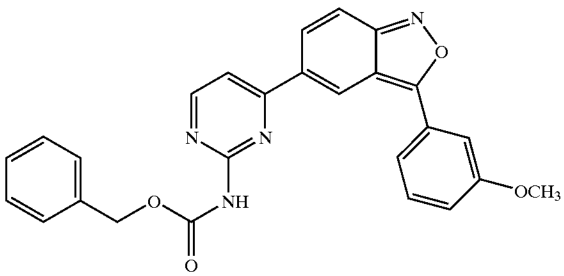 |
| I-A63 | 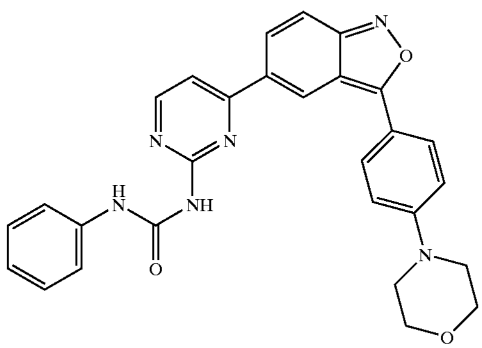 |
| I-A64 | 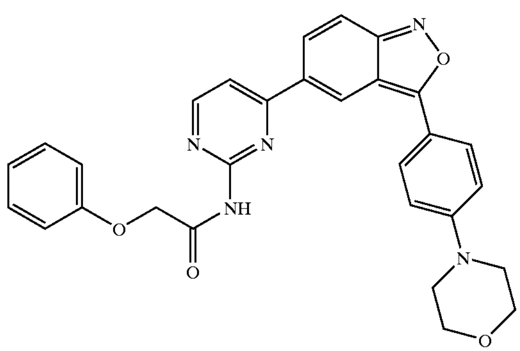 |
| I-A65 | 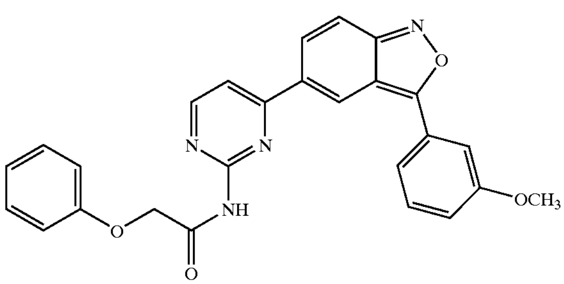 |
| I-A66 | 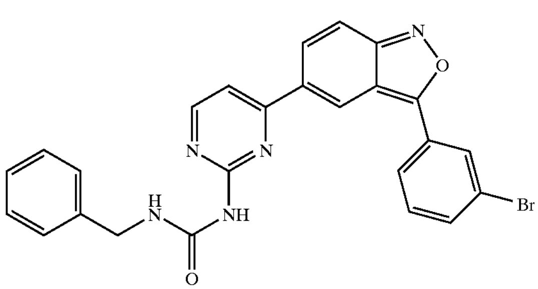 |

-continued
| No. | Structure |
|---|---|
| I-A67 | 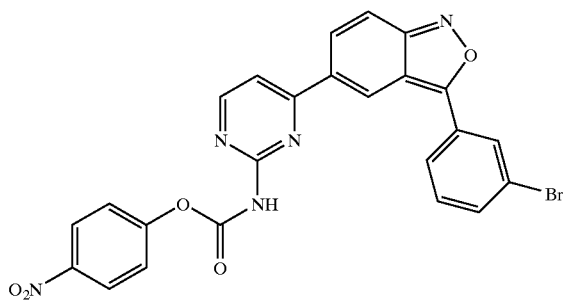 |
| I-A68 | 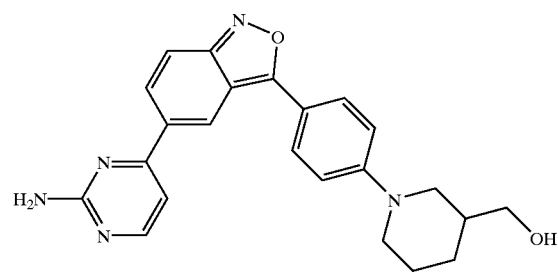 |
| I-A69 | 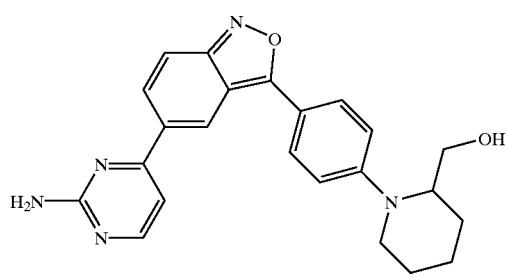 |
| I-A70 | 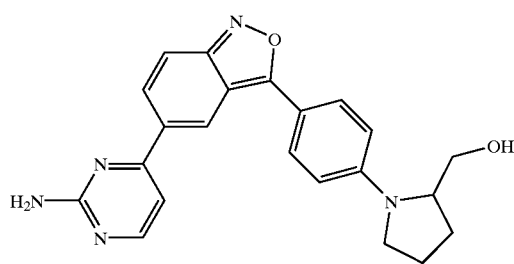 |
| I-A71 | 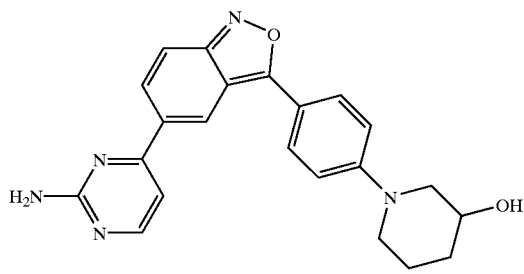 |

| No. | Structure |
|---|---|
| I-A72 | 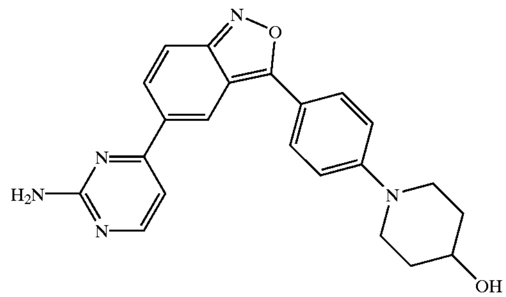 |
| I-A73 | 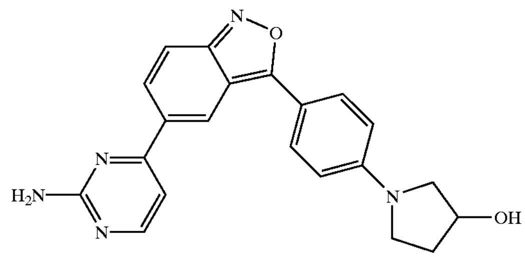 |
| I-A74 | 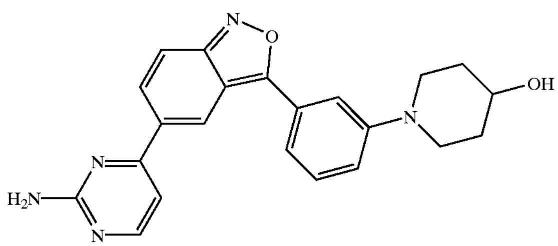 |
| I-A75 | 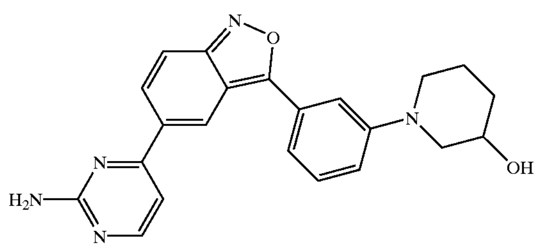 |
| I-A76 | 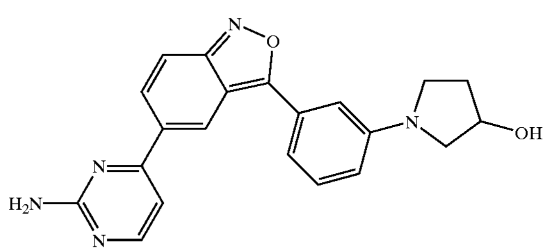 |
| I-A77 | 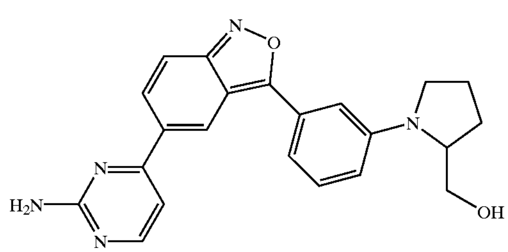 |

-continued
| No. | Structure |
|---|---|
| I-A78 | 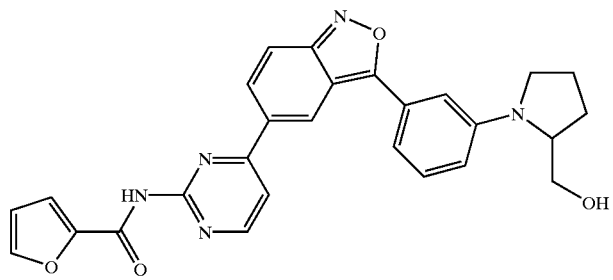 |
| I-A79 | 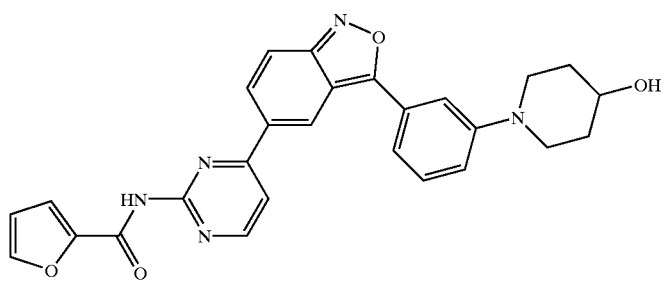 |
| I-A80 | 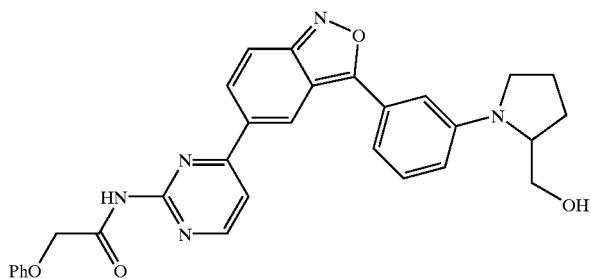 |
| I-A81 | 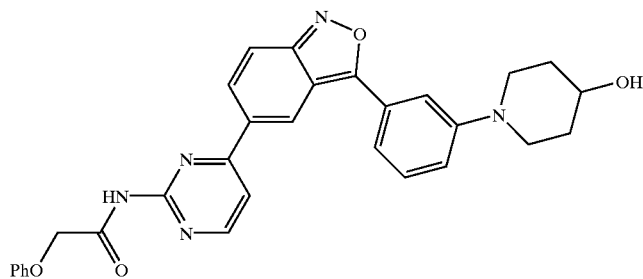 |
| I-A82 | 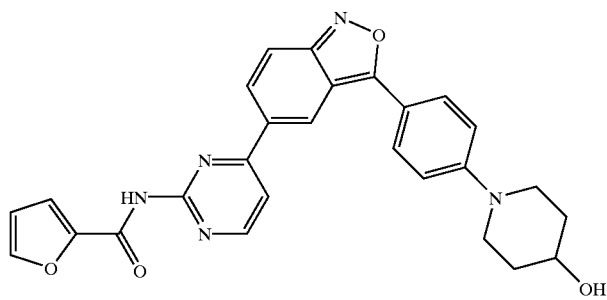 |

-continued

| No. | Structure |
|---|---|
| I-A83 | 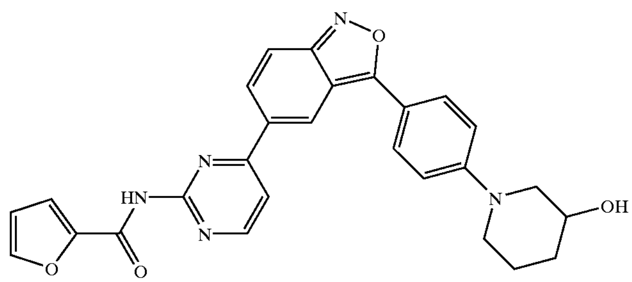 |
| I-A84 | 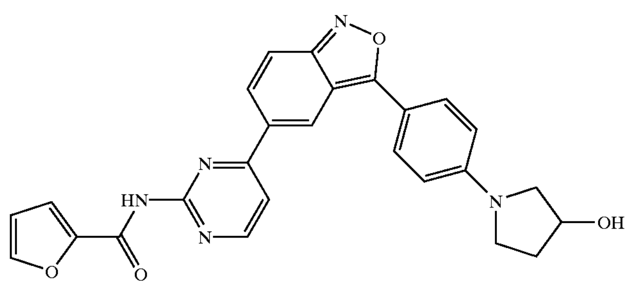 |
| I-A85 | 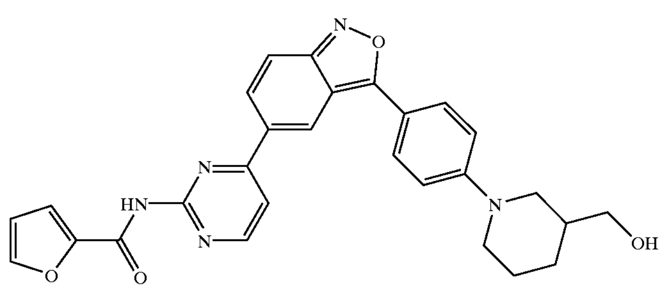 |
| I-A86 | 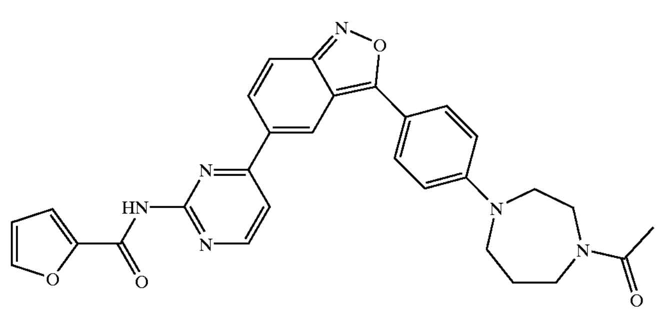 |
| I-A87 | 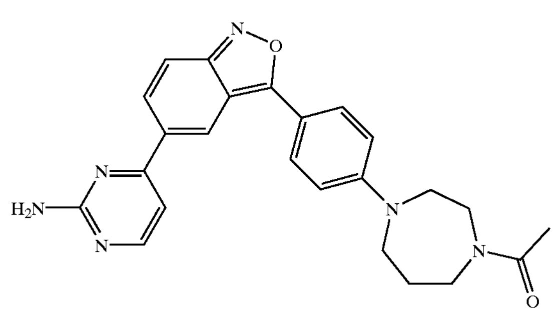 |

-continued

| No. | Structure |
|---|---|
| I-A88 | 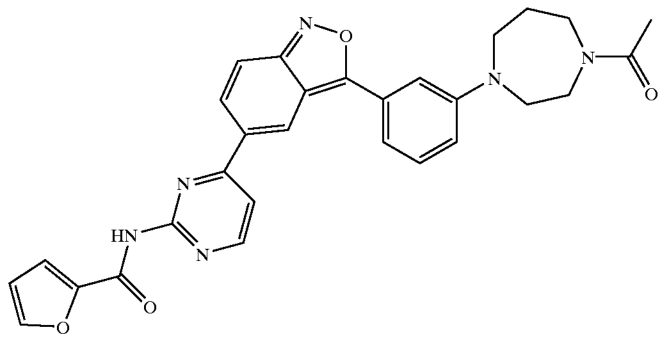 |
| I-A89 | 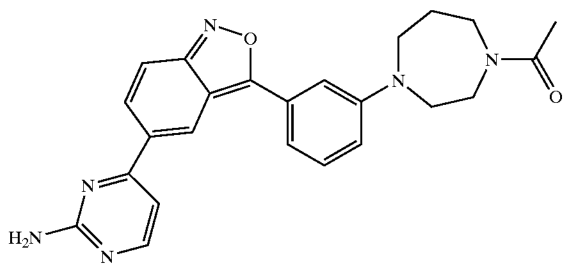 |

10. A composition comprising a compound according to claim 1, and a pharmaceutically acceptable carrier, adjuvant or vehicle.

11. A method of inhibiting GSK-3 or JAK kinase activity in a biological sample, comprising the step of contacting said biological sample with:

a) a composition according to claim 10; or b) a compound according to claim 1.

12. A method of treating an allergic or type I hypersensitivity reaction, asthma, transplant rejection, graft versus host disease, rheumatoid arthritis, amyotrophic lateral sclerosis, multiple sclerosis, Familial amyotrophic lateral sclerosis (FALS), leukemia, or lymphoma in a patient, wherein said method comprises administering to said patient a composition according to claim 10.

13. A method of treating diabetes or schizophrenia in a patient, wherein said method comprises administering to said patient a composition according to claim 10.

* * * * *